(12) United States Patent
Casasanta, III et al.

(10) Patent No.: US 10,004,885 B2
(45) Date of Patent: Jun. 26, 2018

(54) IMAGING APPLICATOR FOR TREATING SKIN CONDITIONS

(71) Applicant: L'Oreal, Paris (FR)

(72) Inventors: Vincenzo Casasanta, III, Woodinville, WA (US); Joseph W. Grez, North Bend, WA (US); Zane Bowman Allen Miller, Seattle, WA (US)

(73) Assignee: L'Oreal, Paris (FR)

( * ) Notice: Subject to any disclaimer, the term of this patent is extended or adjusted under 35 U.S.C. 154(b) by 475 days.

(21) Appl. No.: 14/720,296

(22) Filed: May 22, 2015

(65) Prior Publication Data
US 2016/0339220 A1 Nov. 24, 2016

(51) Int. Cl.
*A61M 35/00* (2006.01)

(52) U.S. Cl.
CPC ....... *A61M 35/003* (2013.01); *A61M 2210/04* (2013.01)

(58) Field of Classification Search
CPC ........ A61M 35/003; A61M 2205/3317; A61M 2205/3379; A61M 2210/04; A45D 34/041; A45D 2044/007
See application file for complete search history.

(56) References Cited

U.S. PATENT DOCUMENTS

| 8,464,732 B2 | 6/2013 | Wong |
| 2004/0186373 A1 | 9/2004 | Dunfield |
| 2006/0210132 A1* | 9/2006 | Christiansen, II ... A61B 5/0059 382/128 |
| 2008/0146970 A1 | 6/2008 | Litman et al. |
| 2010/0224211 A1 | 9/2010 | Rabe et al. |
| 2011/0270200 A1 | 11/2011 | Edgar et al. |

(Continued)

FOREIGN PATENT DOCUMENTS

| EP | 1 459 782 A2 | 9/2004 |
| EP | 2 314 245 A1 | 4/2011 |

(Continued)

OTHER PUBLICATIONS

The Physics Classroom, Visible Light and the Eye's Response, www.physicsclassroom.com/class/light/Lesson-2/Visible-Light-and-the-Eye-s-Response.*

(Continued)

*Primary Examiner* — Adam Marcetich
*Assistant Examiner* — Jessica Arble
(74) *Attorney, Agent, or Firm* — Christensen O'Connor Johnson Kindness PLLC

(57) ABSTRACT

An applicator includes a discontinuity identification component and at least one treatment composition component. The discontinuity identification component is operably coupled to an electromagnetic energy interrogation component and the discontinuity identification component is configured to determine a treatment status based on an interrogation response to an electromagnetic energy stimulus indicative of an absorption difference of greater than a target amount. The at least one treatment composition component is operably coupled to the discontinuity component and the at least one treatment composition component is configured to selectively deposit a treatment composition on the portion of skin responsive to one or more inputs from the discontinuity component indicative of a target treatment status.

22 Claims, 18 Drawing Sheets

(56) References Cited

U.S. PATENT DOCUMENTS

| | | | |
|---|---|---|---|
| 2013/0204178 A1 | 8/2013 | Luzon et al. | |
| 2013/0302078 A1* | 11/2013 | Edgar | A45D 44/005 401/5 |
| 2015/0057623 A1* | 2/2015 | Hyde | A61B 5/441 604/290 |
| 2015/0201840 A1* | 7/2015 | Kang | A61B 5/0071 600/476 |

FOREIGN PATENT DOCUMENTS

| | | | | |
|---|---|---|---|---|
| WO | 2009/036925 A1 | 3/2009 | | |
| WO | WO 2009036876 A1 * | 3/2009 | | A61M 11/041 |
| WO | WO 2010004531 A1 * | 1/2010 | | A45D 44/005 |

OTHER PUBLICATIONS

Machine English translation of WO 2009/036876 A1.*
Invitation to Pay Additional Fees and Partial International Search Report dated Aug. 2, 2016, issued in corresponding International Application No. PCT/US2016/033358, filed May 19, 2016, 9 pages.
Barreras, F., et al., "Transient High-Frequency Ultrasonic Water Atomization," Experiments in Fluids 33(3):405-413, Sep. 2002.
Dobrev, H., "Fluorescence Diagnostic Imaging in Patients With Acne," Photodermatology, Photoimmunology & Photomedicine 26(6):285-289, Dec. 2010.
Maehara, N., et al., "Influence of the Vibrating System of a Multipinhole-Plate Ultrasonic Nebulizer on Its Performance," Review of Scientific Instruments 57(11):2870-2876, Nov. 1986.
Nielsen K.P., et al., "Reflectance Spectra of Pigmented and Nonpigmented Skin in the UV Spectral Region," Photochemistry and Photobiology 80(3):450-455, Nov.-Dec. 2004.

* cited by examiner

IMAGING APPLICATOR FOR TREATING SKIN CONDITIONS

CROSS-REFERENCES TO RELATED APPLICATIONS

The present application is related to U.S. patent application Ser. No. 14/720,217, entitled "ROLLING APPLICATOR FOR TREATING SKIN CONDITIONS," filed herewith, and to U.S. patent application Ser. No. 14/720,260, entitled "POINT APPLICATOR FOR TREATING SKIN CONDITIONS," the contents of both of which are hereby incorporated by reference in their entirety.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, an applicator includes a discontinuity identification component and at least one treatment composition component. The discontinuity identification component is operably coupled to an electromagnetic energy interrogation component and the discontinuity identification component is configured to determine a treatment status based on an interrogation response to an electromagnetic energy stimulus indicative of an absorption difference of greater than a target amount. The at least one treatment composition component is operably coupled to the discontinuity component and the at least one treatment composition component is configured to selectively deposit a treatment composition on the portion of skin responsive to one or more inputs from the discontinuity component indicative of a target treatment status.

In one example of the applicator, an interrogation response includes spatially resolved image information, or temporally resolved image information. In one example, the absorption difference is greater than 20%. In one example, the discontinuity identification component is operably coupled to one or more electromagnetic energy transducers. In one example, the discontinuity identification component is operably coupled to one or more components having circuitry configured to acquire one or more spatially resolved images the portion of skin. In one example, the discontinuity identification component is operably coupled to one or more components having circuitry configured to acquire one or more temporally resolved images the portion of skin. In one example, the discontinuity identification includes one or more components having circuitry configured to classify an imaged object based on one or more inputs from the discontinuity component indicative of a target treatment status.

In another example of the applicator, a treatable region of interest on the portion of skin will fluoresce at a fluorescence wavelength of electromagnetic energy and the electromagnetic energy interrogation component is configured to receive electromagnetic energy at the fluorescence wavelength. In one example, the applicator includes an illumination source configured to emit electromagnetic energy at a plurality of different peak emission wavelengths. The applicator includes an illumination source that includes a first plurality of illumination sources configured to emit electromagnetic energy at a first wavelength and a second plurality of illumination sources configured to emit electromagnetic energy at a second wavelength.

In another example of the applicator, the applicator further includes a display arranged on the applicator in a direction that is different from a direction that electromagnetic energy is directed from an illumination source. In one example, the display is configured to display an indication of a reduction in size of a treatable region of interest from a time before a previous treatment of the treatable region of interest. In one example, the display is configured to display an indication of a treatable region of interest based on the electromagnetic energy received by the electromagnetic energy interrogation component from the portion of skin. In one example, the indication of the treatable region of interest is an image of the treatable region of interest at a scale that is larger than an actual size of the treatable region of interest. In one example, the at least one treatment composition component includes a plurality of treatment components configured to selectively deposit a plurality of treatment compositions. In one example, the controller is further configured to select, from the plurality of treatment compositions, the treatment composition to be deposited on the portion of skin based in part on the characteristic of electromagnetic energy received by the imaging component from the portion of skin. In one example, the illumination source is configured to emit electromagnetic energy in a range from about 200 nm to about 2000 nm.

In another embodiment, a method of treating a portion of skin using an applicator includes receiving an electromagnetic energy response from the portion of skin interrogated with an electromagnetic energy stimulus, determining discontinuity identification information responsive to receiving the electromagnetic energy response from the portion of skin, and selectively depositing a treatment composition to a region of interest on the portion of skin when determining discontinuity identification information is indicative of a target treatment status.

In one example of the method, the method includes determining that the electromagnetic energy response from the portion of skin is associated with a treatable region of interest on the portion of skin and determining a difference between a characteristic of the electromagnetic response from the portion of skin and a corresponding characteristic of electromagnetic energy stimulus emitted toward the portion of skin. In another example, the difference between the electromagnetic energy response from the portion of skin and the corresponding characteristic of the electromagnetic energy stimulus emitted toward the portion of skin is one or more of a difference in wavelength or a difference in color. In another example, the method further includes determining a baseline characteristic of the portion of skin. In another example, the method further includes determining a difference between the electromagnetic energy response from the portion of skin and the baseline characteristic of the portion of skin.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

Figure 1:
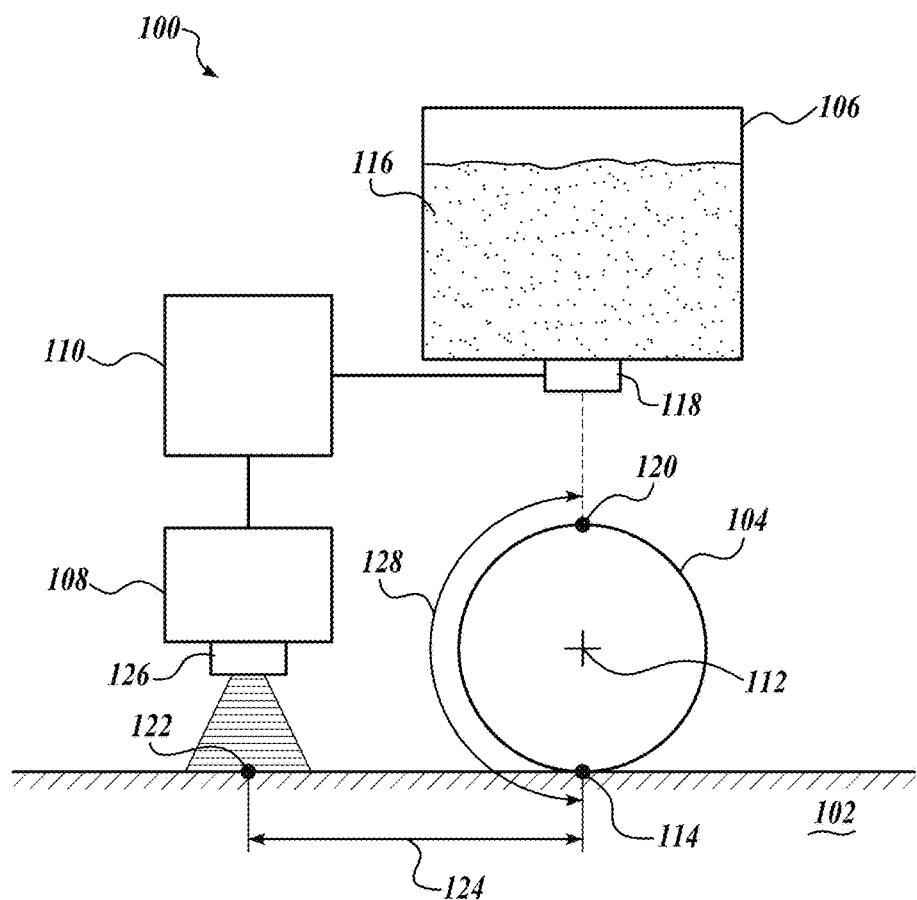
FIG. 1 depicts an embodiment of a rolling applicator used to treat a portion of skin.

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The appearance of smooth and uniform skin is affected by a number of factors. Blemishes or patches sometimes occur within the epidermis and dermis. These blemishes or patches are typically spatially-distinct manifestations of any number of conditions. Some examples of these conditions include pimples (open or closed comedones), hyperpigmentation (i.e., melasma), sun related age spots (solar lentigines), and several types of benign keratosis.

Traditionally, the treatment of localized skin features has involved the uniform application of a treatment composition. Chemical peels involving a variety hydroxylated carboxylic acids are commonly used for the diminution of localized spots and irregularities. Peels are also performed with trichloroacetic acid, Jessner's solution, phenol, and retinoic acid. Several treatments target hyperpigmentation specifically, such as hydroquinone, tretinoin, and azelaic acid. When applied uniformly, such chemical treatments also act on the normally pigmented areas of the skin or regions that are not in need of any specialized treatment. Since many of these chemicals are quite aggressive and may have some level of toxicity, overuse of these chemicals leads to undue irritation, inflammation, rashes, and discomfort. Therefore, a need exists to reduce the amount of unintended irritation in normal skin regions associated with uniform application of a treatment composition.

The following discussion provides examples of systems, apparatuses, and methods for sensing and treating skin conditions using applicators to apply treatment compositions to select portions of skin. In various embodiments, the treatment compositions described herein are one or more of a cosmetic composition (e.g., makeup, foundation, bronzer, etc.), a medical ointment (e.g., antibacterial ointment, hydrocortisone cream, etc.), a cleanser (e.g., soap, makeup remover, etc.), or any other composition that is capable of being applied to a portion of skin. In various embodiments, a treatment composition is a liquid, a non-Newtonian substance, a gel, or any other type of composition. In other examples, treatment compositions are capable of being selectively deposited onto objects, such as rollers, or directly onto a portion of skin.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Rolling Applicator

The following discussion provides examples of systems, apparatuses, and methods for sensing and treating skin conditions using a rolling applicator that has a roller and a cutaneous measurement component. In one example, a cutaneous measurement component is located away from a roller to generate one or more parameters associated with a portion of skin at least one half of the roller's circumference away from the roller. The one or more parameters are used to control selective depositing of treatment composition on the roller. In some examples described herein, the rolling applicator senses particular regions of interest on a portion of skin and selectively applies treatment composition to the regions of interest.

FIG. 1 depicts an embodiment of a rolling applicator 100 used to treat a portion of skin 102. The rolling applicator 100 includes a roller 104, a treatment composition component 106, a cutaneous measurement component 108, and a controller 110. As the rolling applicator 100 is moved across the portion of skin 102, the roller 104 rotates about an axis 112. The roller 104 contacts the portion of skin 102 at a contact location 114. The contact location 114 remains fixed with respect to the axis 112 as the roller 104 rotates about the axis 112 (i.e., the contact location 114 is not a particular location on the surface of the roller 104, but is the location where the roller 104 contacts the portion of skin 102 regardless of any rotation of the roller 104). The roller 104 has a circumference. In one embodiment, the circumference is measured as the distance around a cross-section of the roller 104 that is perpendicular to the axis 112 and passes through the contact location 114. Several embodiments of rollers that are capable of being used as roller 104 in rolling applicator 100 are depicted in FIGS. 2A to 2D.

Figure 2B:
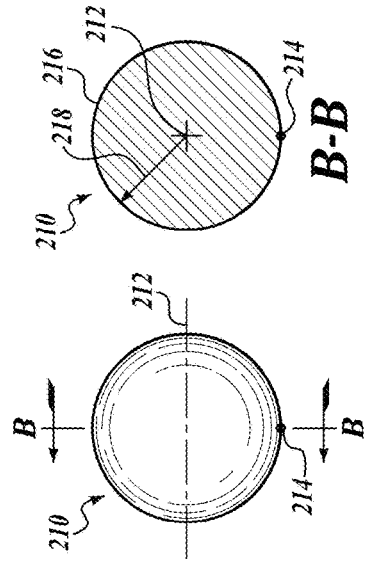
FIGS. 2A to 2D depict embodiments of rollers capable of individually being used as the roller in the rolling applicator depicted in FIG. 1.
Figure 2D:
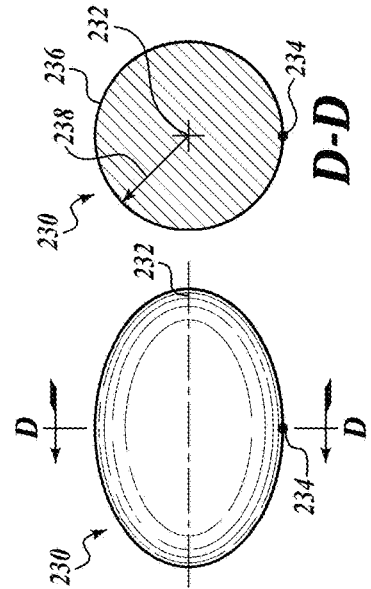
Figure 2A:
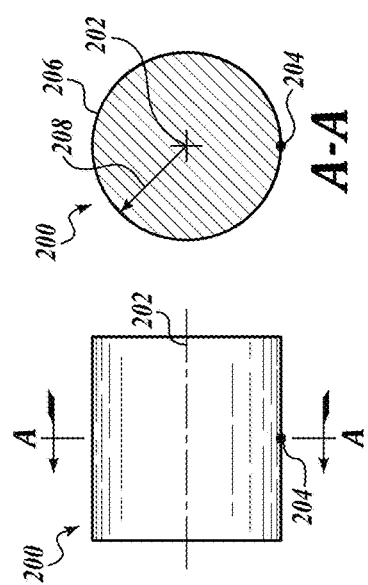

FIG. 2A depicts a front view and a side cross-sectional view of an embodiment of a roller 200 that has a cylindrical shape. The roller 200 rotates about an axis 202 and contacts a portion of skin at a contact location 204. The cross-sectional view of the roller 200 is perpendicular to the axis 202 and passes through the contact location 204. The roller 200 has a circumference 206 that, in one embodiment, is calculated as a function of the radius 208 from the axis 202 at the contact location 204 (i.e., $C=2\pi r$, where C is the circumference 206 at the contact location 204 and r is the radius 208 from the axis 202 at the contact location 204). In the case of the cylindrical roller 200, any cross-section of the roller 200 that is perpendicular to the axis 202 has a radius that is the same length as the radius 208 from the axis 202 at the contact location 204.

FIG. 2B depicts a front view and a side cross-sectional view of an embodiment of a roller 210 that has a spherical shape. The roller 210 rotates about an axis 212 and contacts a portion of skin at a contact location 214. The cross-sectional view of the roller 210 is perpendicular to the axis 212 and passes through the contact location 214. The roller 210 has a circumference 216 that, in one embodiment, is calculated as a function of the radius 218 from the axis 212 at the contact location 214 (i.e., $C=2\pi r$, where C is the circumference 216 at the contact location 214 and r is the radius 218 from the axis 212 at the contact location 214). In the case of the spherical roller 210, a cross-section of the roller 210 that is perpendicular to the axis 212 but at a location other than the contact location 214 will have a radius that is a different length than the radius 218 from the axis 212 at the contact location 214.

Figure 2C:
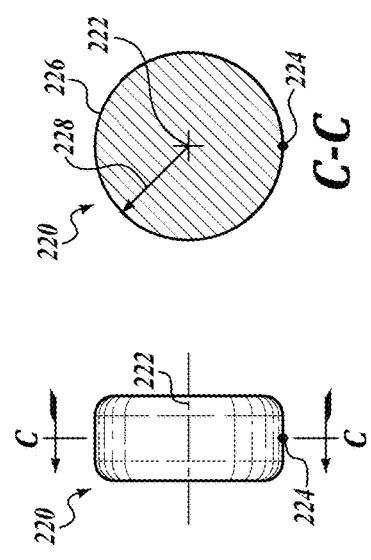

FIG. 2C depicts a front view and a side cross-sectional view of an embodiment of a roller 220 that has a cylindrical shape with rounded edges. The roller 220 rotates about an axis 222 and contacts a portion of skin at a contact location 224. The cross-sectional view of the roller 220 is perpendicular to the axis 222 and passes through the contact location 224. The roller 220 has a circumference 226 that, in one embodiment, is calculated as a function of the radius 228 from the axis 222 at the contact location 224 (i.e., $C=2\pi r$, where C is the circumference 226 at the contact location 224 and r is the radius 228 from the axis 222 at the contact location 224). In the case of the cylindrical roller 220 with rounded corners, a cross-section of the roller 220 that is perpendicular to the axis 222 but at a location other than the contact location 224 will have a radius that may have the same or a different length than the radius 228 from the axis 222 at the contact location 224.

FIG. 2D depicts a front view and a side cross-sectional view of an embodiment of a roller 230 that has an oval shape. The roller 230 rotates about an axis 232 and contacts a portion of skin at a contact location 234. The cross-sectional view of the roller 230 is perpendicular to the axis 232 and passes through the contact location 234. The roller 230 has a circumference 236 that, in one embodiment, is calculated as a function of the radius 238 from the axis 232 at the contact location 234 (i.e., $C=2\pi r$, where C is the circumference 236 at the contact location 234 and r is the radius 238 from the axis 232 at the contact location 234). In the case of the oval roller 230, a cross-section of the roller 230 that is perpendicular to the axis 232 but at a location other than the contact location 234 will have a radius that is a different length than the radius 238 from the axis 232 at the contact location 234.

Referring back to FIG. 1, the treatment composition component 106 holds a treatment composition 116. In various embodiments, the treatment composition 116 is capable of being selectively deposited onto the roller 104. In one example, the treatment composition component includes at least one nozzle 118 that selectively deposits the treatment composition on a deposit location 120. The deposit location 120 remains fixed with respect to the axis 112 as the roller 104 rotates about the axis 112 (i.e., the deposit location 120 is not a particular location on the surface of the roller 104, but is the location where the at least one nozzle 118 deposits treatment composition 116 regardless of any rotation of the roller 104). The treatment composition component 106 is fixed with respect to the axis 112 to the roller 104 such that the contact location 114 remains fixed with respect to the axis 112. The deposit location 120 is a circumferential distance 128 away from the contact location 114. In one example, the deposit location 120 is substantially opposite of the contact location 114 (i.e., the deposit location 120 and the contact location 114 are located approximately at two respective ends of a diameter of the roller 104 that passes through the axis 112). In this example, the circumferential distance 128 is approximately one half of the full circumference of the roller 104.

The cutaneous measurement component 108 is configured to generate one or more parameters associated with the portion of skin 102 that includes a target location 122. The target location 122 is a target distance 124 away from the contact location 114. The target distance 124 is greater than or equal to the circumferential distance 128. The target location 122 is a predetermined direction from the contact location 114 that is an intended direction of movement of the rolling applicator 100 across the portion of skin 102. In the particular embodiment shown in FIG. 1, the predetermined direction is to the left of the contact location 114.

In one embodiment, the cutaneous measurement component 108 includes an imager 126 that generates one or more parameters in the form of image data of the portion of skin 102. Representative parameters include parameters about absorbance of electromagnetic energy, reflectance of electromagnetic energy, wavelengths of electromagnetic energy, and the like. In one example, the one or more parameters are determined from image data of one or more pixels generated by the imager 126. In other examples, the parameter is determined from one or more of a direct wavelength measurement or a measurement of a color on a color model (e.g., the RGB [red, green, blue] color model, the CMY [cyan, magenta, yellow] or CMYK [cyan, magenta, yellow, black]

color space, and the like). In various examples, the imager 126 is any type of image sensor, such as a charge-coupled device (CCD) camera or a complementary metal-oxide-semiconductor (CMOS) camera. The imager 126 senses any type of electromagnetic radiation, such as visible light, infrared electromagnetic radiation, ultraviolet electromagnetic radiation, and the like. Various features of image sensors are well-known to one of ordinary skill in the art and will not be discussed in detail here. The imager 126 discriminates color using selective filtering, wavelength selective absorption within multiple photodetector layers, or any other method.

Figure 3:
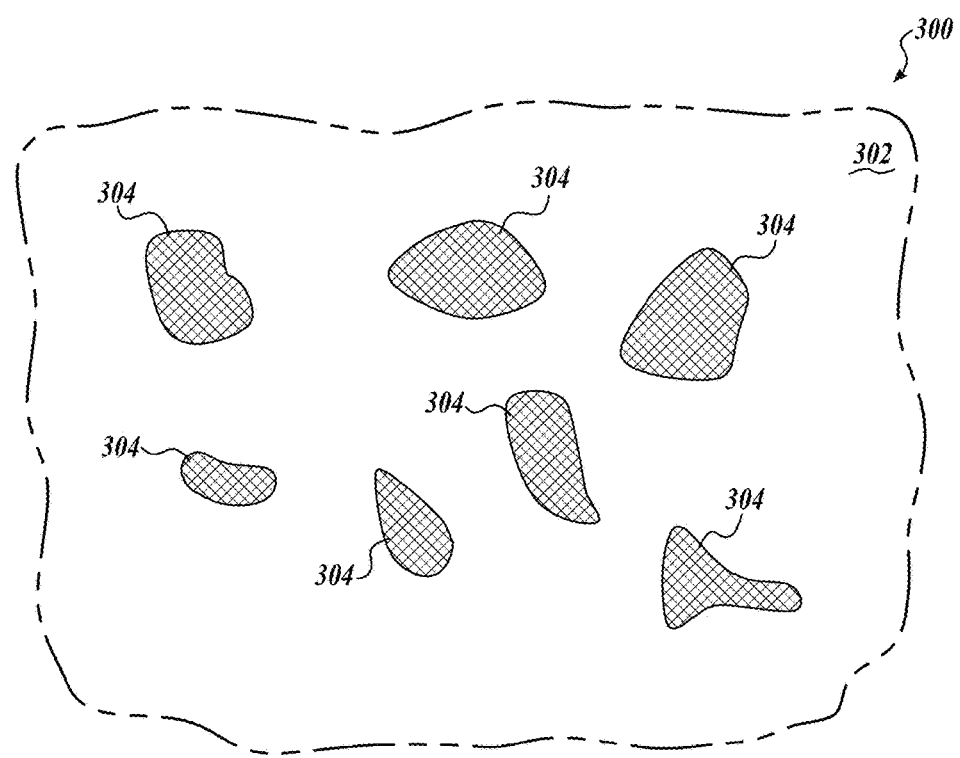
FIG. 3 depicts an example of image data of a portion of skin generated by cutaneous measurement components described herein.

The imager 126 generates image data representing a two-dimensional area of the portion of skin 102. FIG. 3 depicts an example of image data 300 generated by the imager 126. The image data 300 includes background 302 and regions of interest (ROIs) 304. In general, ROIs are blemishes, patches, spots, discolorations, or regions of localized conditions that occur within the epidermis and dermis. ROIs are spatially distinct manifestations of any number of conditions. Examples of those conditions include pimples (open or closed comedones), hyperpigmentation (i.e., melasma), sun-related age spots (solar lentigines), and several types of benign keratosis.

Referring back to FIG. 3, the background 302 represents normal pigments or colors of the portion of skin 102 and the ROIs 304 represent areas of the portion of skin 102 that are treated using the treatment composition 116. The ROIs 304 are determined from the background 302 by selective filtering, by wavelength selective absorption within multiple photodetector layers, or by any other method. In some embodiments, a spectral absorption feature for a given chromophore in skin is manifested as dark spots on an image. In one example, the absorbance and emission characteristics of various skin conditions are included in a library.

Referring back to FIG. 1, the controller 110 is coupled to cutaneous measurement component 108. The controller 110 receives the image data generated by the cutaneous measurement component 108. Using the example of image data 300 from FIG. 3, the controller 110 determines the ROIs 304 from the background 302 of the image data 300. In some embodiments, the controller 110 determines a particular skin condition associated with one or more of the ROIs 304 using the library of absorbance and emission characteristics of various skin conditions described above. The controller 110 is also coupled to the at least one nozzle 118. The controller 110 sends control signals to the at least one nozzle 118 to control the selective depositing of the treatment composition 116 on the deposit location 120 by the at least one nozzle 118. The control signals sent from the controller 110 to the at least one nozzle 118 are based at least in part on the image data 300. In the embodiment shown in FIG. 1, the controller 110 is separate from both the cutaneous measurement component 108 and the at least one nozzle 118. In one alternative embodiment, the controller 110 is part of the cutaneous measurement component 108 and the control signals are sent from the cutaneous measurement component 108 to the at least one nozzle 118. In another alternative embodiment, the controller 110 is part of the at least one nozzle 118 and the image data is sent from the cutaneous measurement component 108 to the at least one nozzle 118.

As noted above, the cutaneous measurement component 108 is configured to generate one or more parameters of the portion of skin 102 that includes a target location 122 and the target location 122 is a target distance 124 that is equal to or greater than the circumferential distance 128. The target distance 124 allows the one or more parameters to be analyzed by the controller 110, the controller 110 to send a control signal to the at least one nozzle 118, and the at least one nozzle 118 to deposit treatment composition 116 onto the roller 104 at the deposit location 120 such that, when the roller 104 is rolled to the target location 122, the treatment composition 116 is applied to the portion of skin 102 at the appropriate location. An example of such an operation is shown in FIGS. 4A to 4D.

FIGS. 4A to 4D depict an embodiment of a rolling applicator 400, in accordance with the other rolling applicators described herein, for applying treatment composition to a portion of skin 402. The rolling applicator 400 includes a roller 404, a treatment composition component 406, a cutaneous measurement component 408, and a controller 410. The rolling applicator 400 is moved from right to left, causing the roller 404 to rotate in a counterclockwise direction over the portion of skin 402, as shown by the arrows in FIGS. 4A to 4D. The cutaneous measurement component 408 is positioned to generate one or more parameters of a target location of the portion of skin 402 that is a target distance away from a contact location between the roller 404 and the portion of skin 402. The target distance is equal to or greater a circumferential distance between the contact location and a deposit location on a surface of the roller 404. Each of FIGS. 4A to 4D depicts an instance in a sequence of instances of using the rolling applicator 400 to apply treatment composition to the portion of skin 402.

Figure 4A:
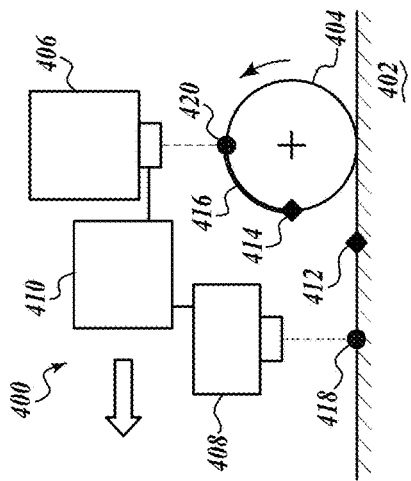
FIGS. 4A to 4D depict an embodiment of a process of using embodiments of the rolling applicators described herein.

At the instant shown in FIG. 4A, the cutaneous measurement component 408 is located over a first target location 412. The cutaneous measurement component 408 generates one or more parameters associated with a first target location 412. The one or more parameters associated with a first target location 412 are sent from the cutaneous measurement component 408 to the controller 410. The controller 410 generates a control signal based at least in part on the one or more parameters associated with a first target location 412 and sends the control signal to the treatment composition component 406. In the particular instance depicted in FIG. 4A, the control signal indicates that treatment composition from the treatment composition component 406 should be deposited onto the roller 404 at a first roller location 414. The treatment composition component 406 begins depositing treatment composition onto a first roller location 414 on the roller 404.

Figure 4B:
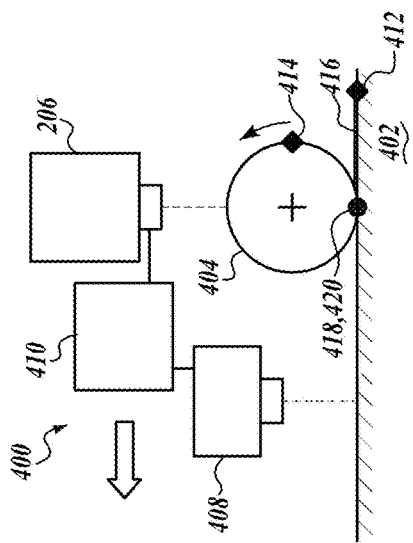

At the instant depicted in FIG. 4B, the cutaneous measurement component 408 is located over a second target location 418 and the roller 404 has moved closer to the first target location 412. In the time between the instances depicted in FIGS. 4A and 4B, the cutaneous measurement component 408 continued to generate one or more parameters associated with the portion of skin 402 between the first target location 412 and the second target location 418, and the controller 410 continues to generate a control signal based at least in part on the image data and sends the control signal to the treatment composition component 406. In the particular example depicted in FIGS. 4A and 4B, the control signal indicated that treatment composition from the treatment composition component 406 should be deposited onto the roller 404 between the first roller location 414 and a second roller location 420. In one embodiment, such a control signal is based on a determination by the controller 410 that a treatable ROI is located on the portion of skin 402 between the first target location 412 and the second target location 418. As shown in FIG. 4B, treatment composition 416 is located on the surface of the roller 404 between the first roller location 414 and the second roller location 420.

At the instant depicted in FIG. 4B, the controller 410 determines that treatment of the portion of skin 402 is not needed beyond the second target location 418 and sends a control signal to the treatment composition component 406 to cease depositing treatment location on the roller 404.

Figure 4C:
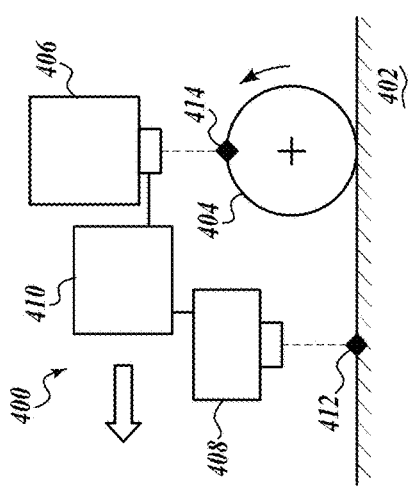

At the instant depicted in FIG. 4C, the rolling applicator 400 has been moved further to the left and the roller 404 has rolled over the portion of skin 402 until the first roller location 414 contacts the first target location 412. At this point, the treatment composition 416 on the roller 404 begins to be transferred to the portion of skin 402. In one embodiment, a surface of the roller 404 is made of a material that allows the treatment composition 416 to remain on the surface of the roller 404 when the treatment composition 416 is deposited by the treatment composition component 406, but also allows most or all of the treatment composition 416 to be transferred to the portion of skin 402 when the portion of the roller 404 with the treatment composition 416 comes into contact with the portion of skin 402. In one embodiment, the surface of the roller 404 has a texture similar to clean, healthy skin. In this embodiment, when the treatment composition 416 is transferred from the surface of the roller 404 to the portion of skin 402, the transferred treatment composition 416 maintains the texture of the surface of the roller 404 such that the transferred treatment composition 416 appears like clean, healthy skin.

Figure 4D:
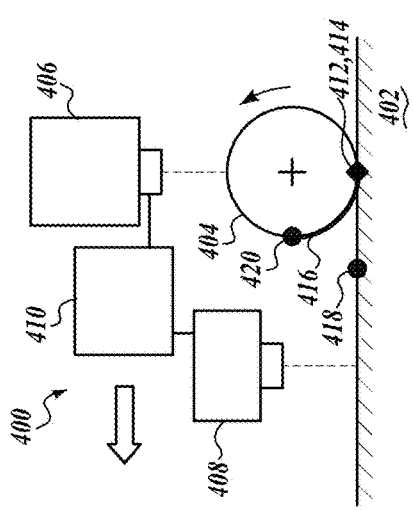

At the instant depicted in FIG. 4D, the rolling applicator 400 has been moved even further to the left and the roller 404 has rolled over the portion of skin 402 until the second roller location 420 contacts the second target location 418. The treatment composition 416 that had previously been on the roller 404 (as shown in FIG. 4B) has been transferred to the portion of skin 402 between the first target location 412 and the second target location 418. One benefit of the user of the rolling applicator 400 is shown in FIG. 4D where the treatment composition 416 has been applied to the portion of skin 402 between the first target location 412 and the second target location 418. As described above, a treatable ROI may exist on the portion of skin 402 between the first target location 412 and the second target location 418. The rolling applicator 400 has applied treatment composition 416 to the treatable ROI without over-applying treatment composition to areas of the portion of skin 402 outside of the ROI. In addition, the rolling applicator 400 applied treatment composition 416 to the entire treatable ROI without under applying treatment composition 416 by missing a portion of the treatable ROI. In other embodiments, the rolling applicator 400 is operated continuously, applying treatment composition 416 to skin conditions encountered as the roller 404 traverses skin.

In the instances depicted in FIGS. 4A to 4D, the rolling applicator 400 is positioned with the cutaneous measurement component 408 over a target location on the portion of skin at a target distance away from the contact location between the roller 404 and the portion of skin 402. The target distance is about equal to a circumferential distance between the contact location between the roller 404 and the portion of skin 402 and a deposit location at which the treatment composition component 406 deposits treatment composition 416 onto the roller 404. In this embodiment, the time between the cutaneous measurement component 408 generating the image data and the treatment composition component 406 depositing the treatment composition is minimal. To a user of the rolling applicator 400, it may appear that the treatment composition component 406 depositing the treatment composition simultaneously with or immediately after the cutaneous measurement component 408 generates the one or more parameters. In another embodiment, the target distance is greater than the circumferential distance. Such an arrangement allows for a delay between the time that the cutaneous measurement component 408 generates the one or more parameters and the treatment composition component 406 deposits the treatment composition. This delay allows time for the controller 410 to process the image data before the treatment composition component 406 deposits the treatment composition.

Figure 5A:
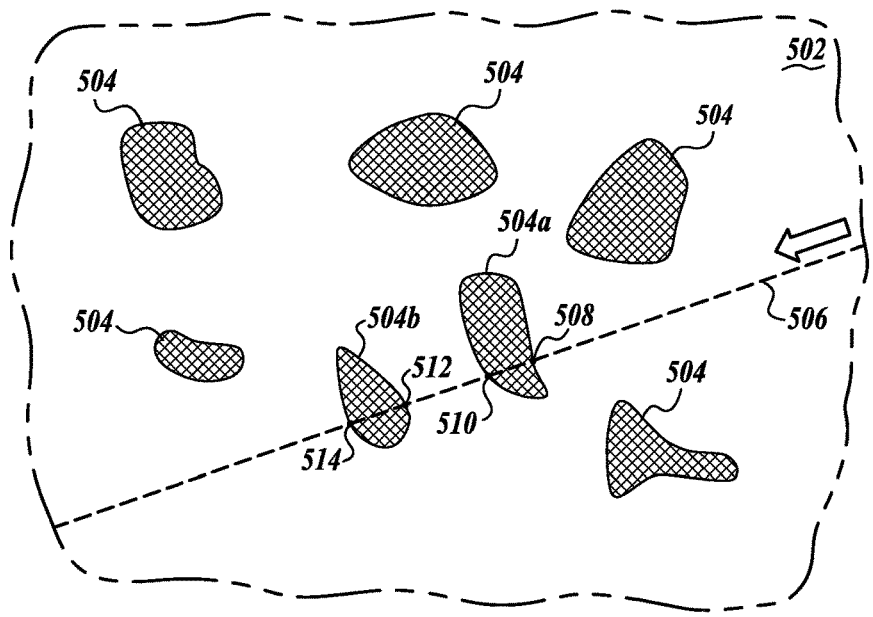
FIGS. 5A and 5B depict examples of movement of a rolling applicator, in accordance with embodiments of the rolling applicators disclosed herein, over a portion of skin.

Movement of a rolling applicator, in accordance with embodiments of the rolling applicators disclosed herein, over a portion of skin 502 is depicted in FIG. 5A. The portion of skin 502 includes a number of ROIs 504. The ROIs 504 include two particular ROIs 504a and 504b. The rolling applicator includes a roller and a cutaneous measurement component, in accordance with other rolling applicators disclosed herein. The cutaneous measurement component is positioned to generate image data of the portion of skin 502 at a distance equal to or greater than a circumferential distance of the roller. The circumferential distance is the distance along the roller surface between the point at which the roller contacts the portion of skin 502 and a deposition point at which a treatment composition component deposits treatment composition on the roller surface.

FIG. 5A depicts a contact line 506 that represents the path of a contact location of the rolling applicator's roller across the portion of skin 502 in a direction from right to left, as indicated by the arrow. The contact line 506 intersects the ROI 504a from point 508 to point 510, and the contact line 506 intersects the ROI 504b from point 512 to point 514. As the rolling applicator is rolled along the contact line 506, the cutaneous measurement component of the rolling applicator will generate one or more parameters and a controller will generate control signals based at least in part on the one or more parameters. The control signals will be sent to the treatment composition component to control selective depositing of treatment composition on the roller.

As the rolling applicator is moved from right to left along the contact line 506, a control signal based at least on the one or more parameters generated by the cutaneous measurement component is sent to a treatment composition component. The control signal causes the treatment composition component to dispense treatment composition onto the deposition location on the roller such that the treatment composition is applied to the ROI 504a between the point 508 and the point 510 as the roller rolls over the ROI 504a. The control signal also causes the treatment composition component to stop dispensing treatment composition onto the roller such that treatment composition is not applied to the portion of skin 502 between the point 510 and the point 512 as the roller rolls over the portion of skin 502 between the ROI 504a and the ROI 504b. The control signal also causes the treatment composition component to dispense treatment composition onto the roller at the deposition location such that the treatment composition is applied to the ROI 504b between the point 512 and the point 514 as the roller rolls over the ROI 504b. The control signal also causes the treatment composition component to stop dispensing treatment composition onto the roller such that treatment composition is not applied to the portion of skin 502 after the point 514.

Figure 5B:
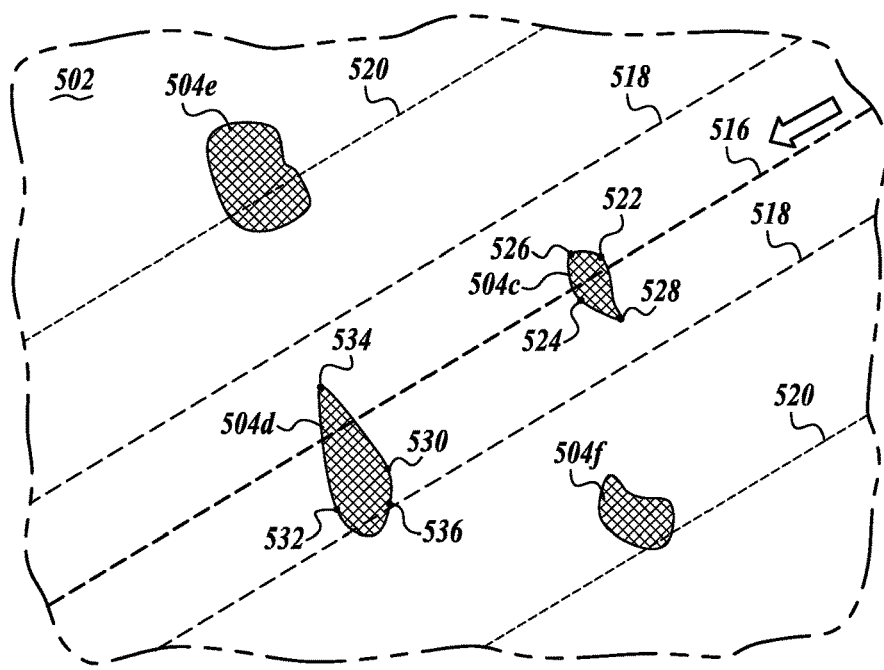

Another example of the use of a rolling applicator on a portion of skin 502 is depicted in FIG. 5B. The portion of skin 502 shown in FIG. 5B includes ROIs 504c to 504f. A contact line 516 passes through the ROIs 504c and 504d. The contact line 516 represents the path of a contact location of the rolling applicator's roller across the portion of skin 502 in a direction from right to left, as indicated by the arrow. FIG. 5B also shows roller width lines 518 and measurement width lines 520. The roller width lines 518 are indications of the extents of the width that the roller is capable of applying treatment composition to the portion of skin 502. The measurement width lines 520 are indications of the extents of the width that the cutaneous measurement component is capable of generating the one or more parameters (e.g., a width that an image capture device can capture image data in the case where the one or more parameters include image data). In this particular example, the measurement width lines 520 are wider than the roller width lines 518, indicating that the one or more parameters may include information about ROIs that cannot be treated by the roller as is continues along the contact line 516 (e.g., ROIs 504e and 504f).

As the rolling applicator is moved from right to left along the contact line 516, a control signal based at least on the one or more parameters generated by the cutaneous measurement component is sent to a treatment composition component. In some embodiments, the one or more parameters are analyzed by the controller to determine the geometries of the ROIs 504c and 504d that are located at least partially within the roller width lines 518. The control signals sends control signals to the treatment composition component to control selective depositing of treatment composition on the roller such that treatment composition will be applied to the ROIs 504c and 504d.

The one or more parameters about the ROI 504c are analyzed by the controller to determine the geometry of the ROI 504c. In one example, the controller determines the first point 522 at which the roller will contact the ROI 504c, the last point 524 at which the roller will contact the ROI 504c, the farthest right point 526 that the roller will contact the ROI 504c, and the farthest left point 528 that the roller will contact the ROI 504c. In this example, the control signal sent to the treatment composition component causes the treatment composition component to selectively deposit treatment composition on the roller such that a rectangular shape of treatment composition on the portion of skin 502 where the rectangular shape starts at the first point 522, has a width from the farthest right point 526 to the farthest left point 528, and ends at the last point 524. In another example, the controller determines an approximate boundary of the ROI 504c, including any irregular curves of the boundary. In this example, the control signal sent to the treatment composition component causes the treatment composition component to selectively deposit treatment composition on the roller such that the treatment composition has the same approximate boundary determined by the controller.

The one or more parameters about the ROI 504d are analyzed by the controller to determine the geometry of the ROI 504d. For example, the controller determines the first point 530 at which the roller will contact the ROI 504d, the last point 532 at which the roller will contact the ROI 504d, the farthest right point 534 that the roller will contact the ROI 504c, and the farthest left point 536 that the roller will contact the ROI 504d. The farthest left point 536 happens to be lie on the roller width line 518 because the ROI 504d extends beyond the roller width line 518. In this example, the control signal sent to the treatment composition component causes the treatment composition component to selectively deposit treatment composition on the roller such that a rectangular shape of treatment composition on the portion of skin 502 where the rectangular shape starts at the first point 530, has a width from the farthest right point 534 to the farthest left point 536, and ends at the last point 532.

In another example, the controller determines an approximate boundary of the ROI 504d, including any irregular curves of the boundary. In this example, the control signal sent to the treatment composition component causes the treatment composition component to selectively deposit treatment composition on the roller such that the treatment composition has the same approximate boundary determined by the controller, except that the treatment composition may not be applied to the area of the ROI 504d that lies outside of the roller width line 518.

While the above example describes that treatment composition is applied starting at one point and ending at another point, the actual use of a rolling applicator may not be as precise. Although a particular point may be the ideal point to start applying treatment composition, the actual application of the treatment composition may begin near that particular point (either before or after the particular point). Similarly, although a particular point may be the ideal point to stop applying treatment composition, the actual application of the treatment composition may stop near that particular point (either before or after the particular point). In one embodiment, a rolling applicator may be configured to substantially cover a ROI by starting application of the treatment composition before the point at which the roller contacts the ROI and by stopping application of the treatment composition after the point at which the roller stops contacting the ROI.

Figure 6A:
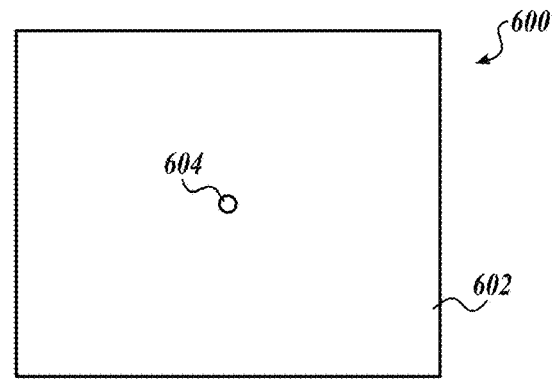
FIGS. 6A to 6C depict various arrangements of nozzles usable in accordance with embodiments of the treatment composition component embodiments described herein.
Figure 6B:
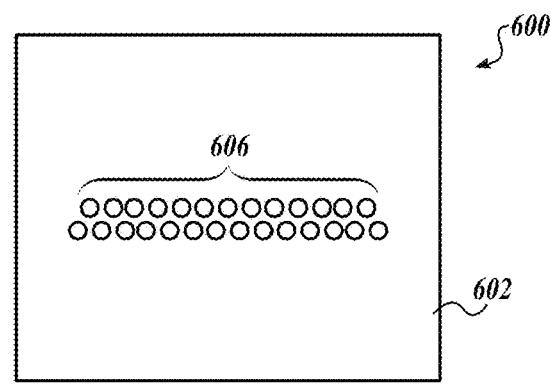
Figure 6C:
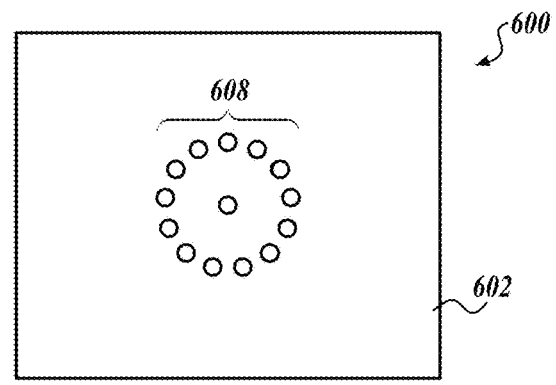

FIGS. 6A to 6C depict a treatment composition component 600 with various arrangements of nozzles on a lower surface 602 of the treatment composition component 600. The lower surface 602 faces a roller such that treatment composition is dispensed from one or more nozzles on the lower surface 602 toward the roller. The various arrangements of nozzles in FIG. 6A to 6C are usable on embodiments of treatment composition components describes herein. Moreover, in other embodiments, any other arrangements of nozzles are used on treatment composition component 600 and/or any of the other embodiments of treatment composition components described herein.

In the embodiment depicted in FIG. 6A, the lower surface includes a nozzle 604 configured to dispense treatment composition from the treatment composition component 600. The single nozzle 604 is located to dispense the treatment composition from the treatment composition component 600 to a particular location along the roller. In the embodiment depicted in FIG. 6B, a number of nozzles 606 are arranged in two rows. The nozzles 606 are arranged to deposit treatment composition across a particular portion of a roller. In one example, the row of nozzles 606 are placed over the cylindrical roller 200 depicted in FIG. 2A such that the nozzles 606 deposit treatment composition along the top of the cylindrical roller 200. Such an arrangement is useful if the width of the treatment composition deposited on the roller varies, such as in the example described above with respect to FIG. 5B. In the depicted embodiment, the two rows of nozzles 606 are offset such that lateral spacing (i.e., spacing from left to right in the depicted view) is smaller than it would be with just one single row. In the embodiment depicted in FIG. 6C, a number of nozzles 608 are arranged in a circular pattern. The nozzles 608 are arranged to deposit treatment composition across a particular portion of a roller. In one example, the circle of nozzles 608 are placed over the spherical roller 210 depicted in FIG. 2B such that the nozzles 608 deposit treatment composition along portions of the top of the spherical roller 210.

In various embodiments, the nozzles 604, 606, and 608 take a number of forms. For example, a diameter of any of the nozzles 604, 606, and 608 is within a range from about 1 micron to about 1 millimeter. The diameter of any of the nozzles 604, 606, and 608 depends on any number of factors, such as the particular application (e.g., the particular region of interest being treated), the treatment composition being dispensed, and the like. Each of the nozzles 604, 606, and 608 includes a propulsion device that dispenses the treatment composition to a roller. Various embodiments of propulsion devices are described in FIGS. 7 and 8.

Figure 7:
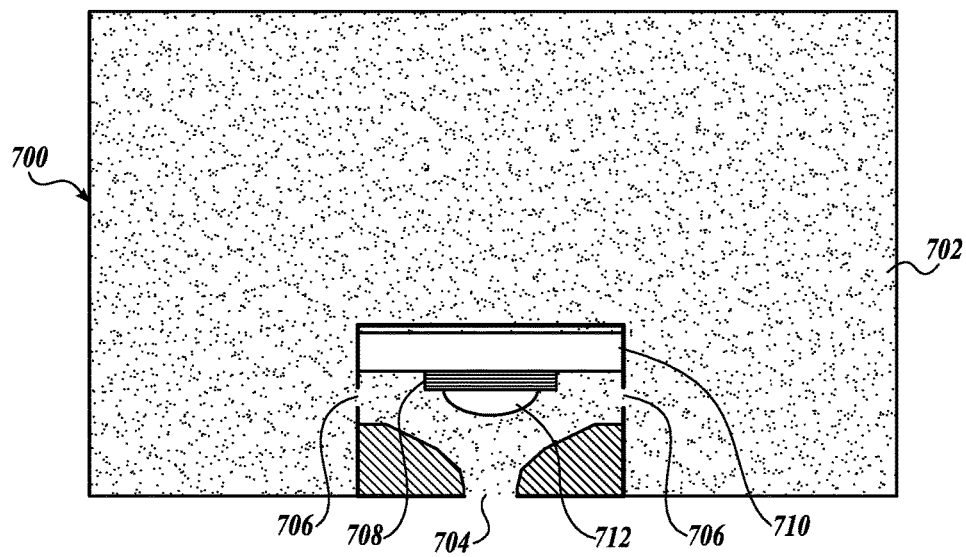
FIG. 7 depicts a cross-sectional view of an embodiment of a thermal propulsion device usable in embodiments of the nozzles described herein to propel treatment composition out of an outlet.

FIG. 7 depicts a cross-sectional view of an embodiment of a thermal propulsion device 700 that is usable in a nozzle to propel treatment composition 702 out of an outlet 704. The treatment composition 702 is located in a treatment composition component, such as in any of the treatment composition components described herein. The treatment composition 702 flows into the thermal propulsion device 700 via one or more inlets 706. The treatment composition 702 flows into the thermal propulsion device 700 via the one or more inlets 706 and out of the outlet 704 continuously such that a continuous flow of treatment composition supplied by the thermal propulsion device 700. The thermal propulsion device 700 also includes a heating element 708 that is supported by a heating substrate 710.

During operation, the heating element 708 produces a localized thermal burst to the treatment composition 702 just above the outlet 704. The localized thermal burst generates a kinetic bubble 712. The burst of the kinetic bubble 712 produces pressure within the thermal propulsion device 700 that propels a droplet of the treatment composition 702 through the outlet 704. In one example, the heating element 708 is heated by electrical pulses and formed of a metallic material with high electrical resistance. The heating substrate 710 contains elements that support the heating element 708, such as a source of power and address circuitry that drives the thermal propulsion device 700 to produce a droplet of treatment composition 702. The heating substrate 710 is in communication with a controller that sends signals to the thermal propulsion device 700 to control when the thermal propulsion device 700 produces a droplet of treatment composition 702. For example, the controller sends a signal to the thermal propulsion device 700 such that the thermal propulsion device 700 produces a droplet of treatment composition 702 at an appropriate time to treat a particular ROI.

Figure 8:
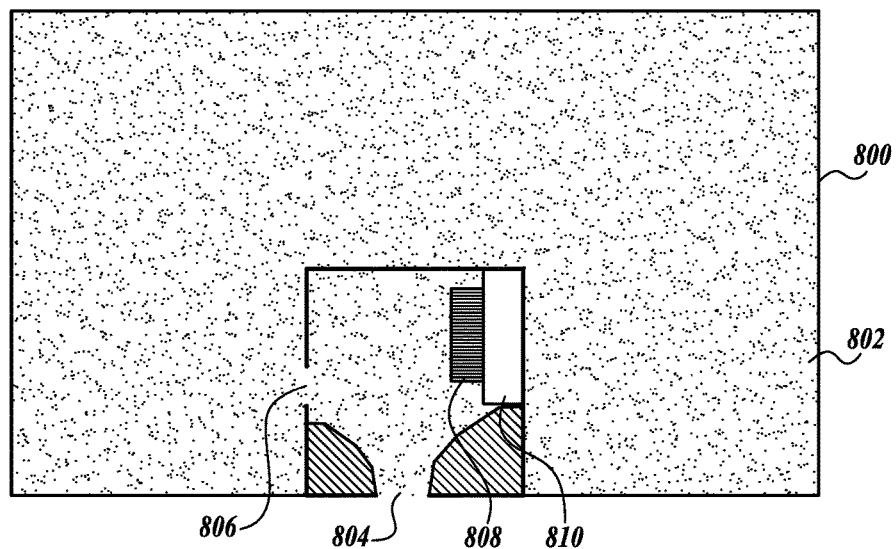
FIG. 8 depicts a cross-sectional view of an embodiment of a transducer propulsion device usable in embodiments of the nozzles described herein to propel treatment composition out of an outlet.

FIG. 8 depicts a cross-sectional view of an embodiment of a transducer propulsion device 800 that is usable in a nozzle to propel treatment composition 802 out of an outlet 804. The treatment composition 802 is located in a treatment composition component, such as in any of the treatment composition components described herein. The treatment composition 802 flows into the transducer propulsion device 800 via one or more inlets 806. The treatment composition 802 flows into the thermal propulsion device 800 via the one or more inlets 806 and out of the outlet 804 continuously such that a continuous flow of treatment composition is supplied by the transducer propulsion device 800. The transducer propulsion device 800 also includes a transducer 808 that is supported by a transducer substrate 810. In one embodiment, the transducer 808 is a piezoelectric transducer.

During operation, the transducer 808 produces a localized and pulsed mechanical displacement to the fluid to the treatment composition 802 within the transducer propulsion device 800. The mechanical displacement produced by the transducer 808 creates pressure within the transducer propulsion device 800 and the pressure propels a droplet of treatment composition 802 through the outlet 804. The mechanical displacement of the transducer 808 is produced by an electrical pulse across the transducer 808. In the example where the transducer 808 is a piezoelectric transducer, the piezoelectric effect causes the transducer 808 to strain (i.e., displace) in response to the electrical pulse. The transducer 808 is formed of a ferroelectric material that possesses a net electric polarization. The transducer substrate 810 contains elements that support the transducer 808, such as a source of power and address circuitry that drives the transducer propulsion device 800 to produce a droplet of treatment composition 802. The transducer substrate 810 is in communication with a controller that sends signals to the transducer propulsion device 800 to control when the transducer propulsion device 800 produces a droplet of treatment composition 802. For example, the controller sends a signal to the transducer propulsion device 800 such that the transducer propulsion device 800 produces a droplet of treatment composition 802 at an appropriate time to treat a particular ROI.

Other propulsion devices, beyond those depicted in FIGS. 7 and 8, are usable with any of the applicators described herein. For example, ultrasonic liquid atomizers, such as is described in U.S. Published Patent Application No. 2010/0044460 A1, which is hereby incorporated by reference in its entirety, are propulsion devices that are usable in embodiments of the applicators described herein. Any other suitable propulsion devices are also usable with embodiments of the applicators described herein to dispense treatment composition.

Figure 9:
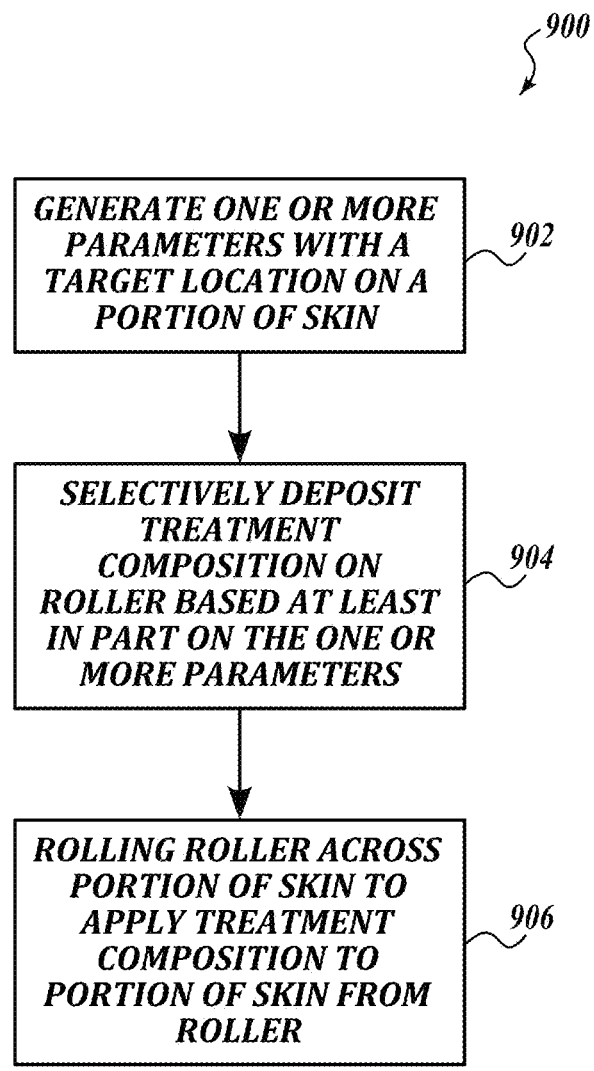
FIG. 9 depicts an embodiment of a method of applying treatment composition to a portion of skin using embodiments of the embodiments of rolling applicators described herein.

Any of the embodiments of rolling applicators described herein are capable of being used to perform a method 900 depicted in FIG. 9. At box 902, one or more parameters associated with a target location of a portion of skin are generated as a roller is rolled across the portion of skin. The one or more parameters are generated by a cutaneous measurement component. The cutaneous measurement component is arranged with respect to the roller such that the target location is a target distance from a contact location where the roller contacts the portion of skin. At block 904, treatment composition is selectively deposited from a treatment composition component onto a roller at a deposit location based at least in part on the one or more parameters. The deposition location is located on the roller a circumferential distance away from the contact location and the target distance is equal to or greater than the circumferential distance.

In some embodiments, the method 900 includes additional steps described herein that are not depicted in FIG. 9. For example, at block 906, the roller of the applicator is rolled across the portion of skin such that the treatment composition selectively deposited on the roller is applied to the portion of skin. In other examples, the method 900 also includes one or more steps, such as identifying a ROI from the one or more parameters, determining a geometry of the ROI, applying the treatment composition from the roller onto the portion of skin as the roller continues to roll across the portion of skin, or any other step described herein.

Point Applicator

The following discussion provides examples of systems, apparatuses, and methods for sensing and treating skin conditions using a point applicator that has an electromagnetic energy detector and at least one treatment composition component. In one example, the electromagnetic energy detector is configured to generate one or more parameters associated with reflection of an electromagnetic energy interrogation stimulus from a portion of skin. In another example, the at least one treatment composition component is configured to selectively deposit a treatment composition at a deposit location on the portion of skin. The one or more parameters are used to control the at least one treatment composition component to selectively deposit the treatment composition to the deposit location on the portion of skin based at least in part on a change of the level of the one or more parameters indicating a decrease in reflection of electromagnetic energy interrogation stimulus from the portion of skin at the deposit location.

Figure 10:
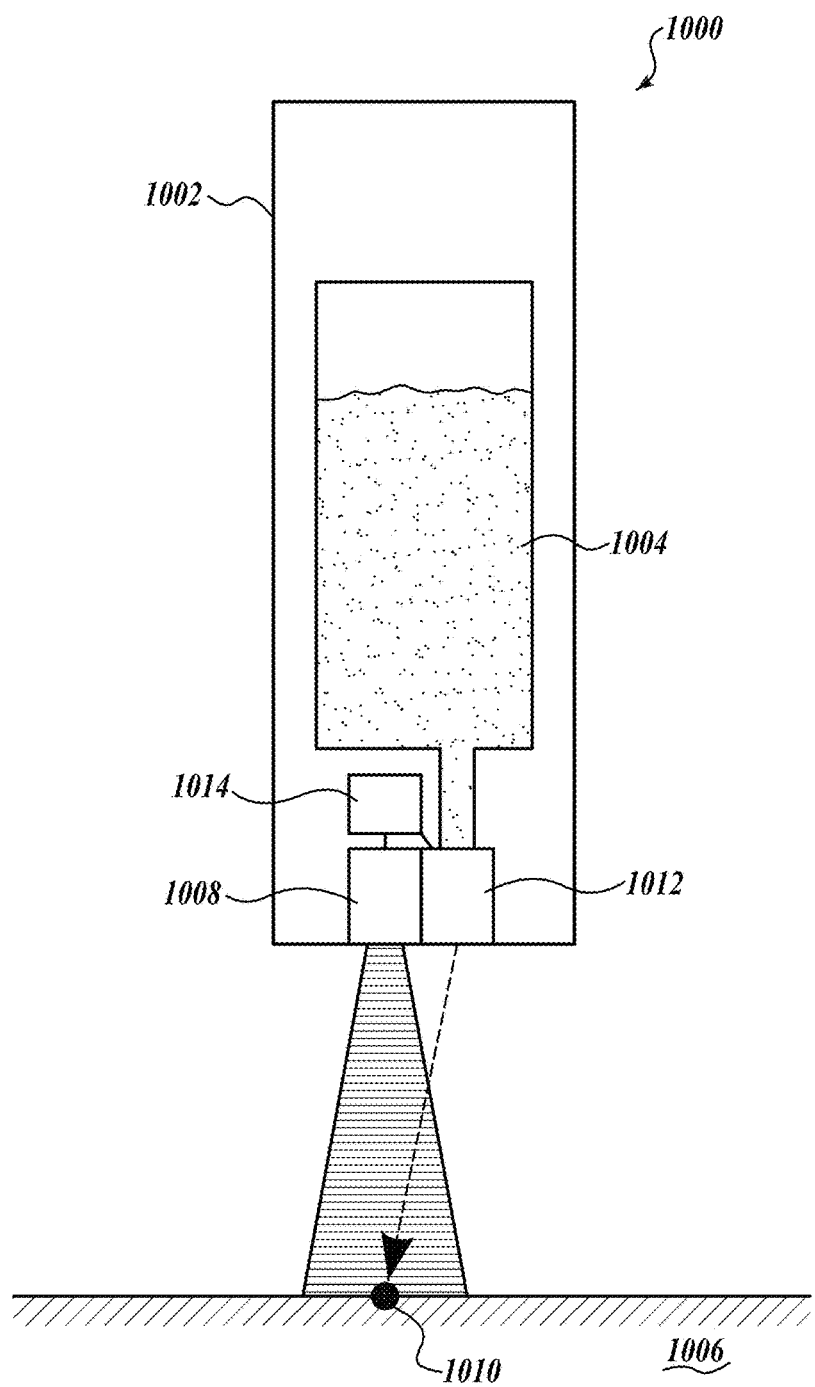
FIG. 10 depicts an embodiment of a point applicator used to treat a portion of skin.

An embodiment of a point applicator 1000 is depicted in FIG. 10. The point applicator 1000 includes a housing 1002 that houses treatment composition 1004 for depositing onto a portion of skin 1006. The point applicator 1000 includes an electromagnetic energy detector 1008 that generates one or more parameters associated with reflection of an electromagnetic energy interrogation stimulus from the portion of skin 1006. In one embodiment, the electromagnetic energy interrogation stimulus is ambient light that is reflected off of the portion of skin 1006. In another embodiment, the electromagnetic energy interrogation stimulus is ambient light that is reflected off of the portion of skin 1006. In yet another embodiment, the electromagnetic energy interrogation stimulus is non-visible light, such as infrared or ultraviolet electromagnetic energy, that is reflected off of the portion of skin 1006. The electromagnetic energy detector 1008 is configured to generate the one or more parameters based on an area of the portion of skin 1006 that includes a deposit location 1010.

The point applicator 1000 also includes a treatment composition component 1012 that is configured to selectively deposit a treatment composition at the deposit location 1010 on the portion of skin 1006. In the embodiment shown in FIG. 10, the point applicator 1000 includes the one treatment composition component 1012, though any number of treatment composition components could be included in the point applicator 1000. The point applicator 1000 also includes a discontinuity identification component 1014 that is coupled to the electromagnetic energy detector 1008 and the treatment composition component 1012. In one embodiment, the discontinuity identification component 1014 is a controller. The discontinuity identification component 1014 monitors a level of the one or more parameters generated by the electromagnetic energy detector 1008 as the applicator 1000 traverses the portion of skin 1006. The discontinuity identification component 1014 also controls the treatment composition component 1012 to selectively deposit the treatment composition to the deposit location 1010 on the portion of skin 1006. In particular, as described in greater detail below, the discontinuity identification component 1014 also controls the treatment composition component 1012 to selectively deposit the treatment composition to the deposit location 1010 based on one or more inputs indicative of a decrease in reflection of electromagnetic energy interrogation stimulus from the portion of skin 1006 at the deposit location 1010.

Figure 11A:
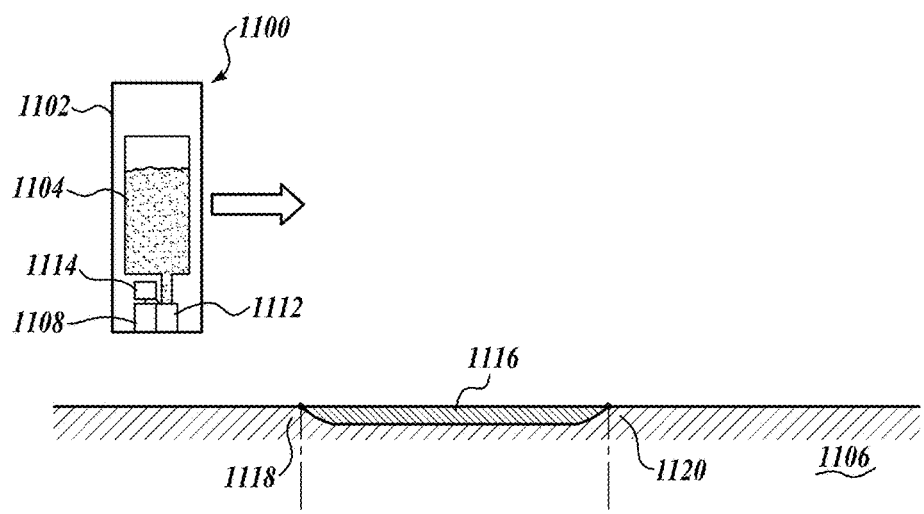
FIGS. 11A and 11B depict, respectively, movement of a point applicator over a portion of skin and a chart showing one example of a level of reflection monitored by the point applicator as it traverses the portion of skin.

Another embodiment of a point applicator 1100 is depicted in FIG. 11A. The point applicator 1100 includes a housing 1102 that houses treatment composition 1104 for depositing onto a portion of skin 1106. The point applicator 1100 includes an electromagnetic energy detector 1108 that generates one or more parameters associated with reflection of an electromagnetic energy interrogation stimulus from the portion of skin 1106. The point applicator 1100 also includes a treatment composition component 1112 that is configured to selectively deposit a treatment composition at a deposit location on the portion of skin 1106. The point applicator 1100 also includes a discontinuity identification component 1114 that is coupled to the electromagnetic energy detector 1108 and the treatment composition component 1112.

In the embodiment shown in FIG. 11A, the point applicator 1100 traverses the portion of skin 1106 from the left to the right, as indicated by the arrow. While the point applicator 1100 traverses the portion of skin 1106, the discontinuity identification component 1114 monitors a level of the one or more parameters generated by the electromagnetic energy detector 1108. The portion of skin 1106 includes a region of interest 1116. In the direction that the point applicator 1100 is moving, the point applicator will encounter a first edge 1118 of the region of interest 1116, pass over the region of interest 1116, and then encounter a second edge 1120 of the region of interest 1116.

Figure 11B:
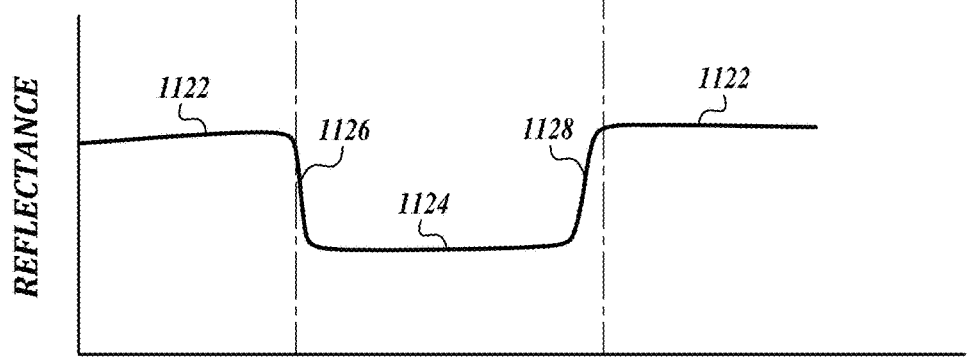

FIG. 11B depicts a chart showing one example of a level of reflection monitored by the discontinuity identification component 1114 as the point applicator 1100 traverses the portion of skin 1106. From each of the left and right sides of the chart, the monitored absorbance level is at a baseline absorbance level 1122. The baseline level absorbance 1122 is measured as the point applicator 1100 traverses the portion of skin 1106 that does not include the region of interest 1116. When the point applicator 1100 is over the middle of the region of interest 1116, the monitored absorbance level is at a lower absorbance level 1124. As the point applicator 1100 is moved from being over the portion of skin 1106 that does not include the region of interest 1116, to being over the first edge 1118, and then being over the region of interest 1116, the monitored absorbance level transitions from the baseline absorbance level 1122 to a decreasing absorbance level 1126 and then to the lower absorbance level 1124. The decreasing absorbance level 1124 may start before, at, or after the point applicator 1100 is over the first edge 1118. As the point applicator 1100 is moved from being over the region of interest 1116, to being over the second edge 1120, and then to being over the portion of skin 1106 that does not include the region of interest 1116, the monitored absorbance level transitions from the lower absorbance level 1124 to an increasing absorbance level 1128 and then to the baseline absorbance level 1122. The increasing absorbance level 1128 may start before, at, or after the point applicator 1100 is over the second edge 1120.

While the point applicator 1100 traverses the portion of skin 1106, the discontinuity identification component 1114 monitors the level of the one or more parameters generated by the electromagnetic energy detector 1108. The discontinuity identification component 1114 identifies the decreasing absorbance level 1124, indicating that a decrease in reflection of electromagnetic energy interrogation stimulus from the portion of skin at a deposit location. In response to identifying, the discontinuity identification component 1114 controls the treatment composition component 1112 to selectively deposit treatment composition 1104 on the deposit location. For example, the discontinuity identification component 1114 sends a signal to the treatment composition component 1112 to control the selective depositing of the treatment composition 1104. In one embodiment, the treatment composition component 1112 deposits a target amount of treatment composition 1104 in response to receiving the signal from the discontinuity identification component 1114. In another embodiment, the treatment composition component 1112 deposits the treatment composition 1104 for a particular amount of time in response to receiving the signal from the discontinuity identification component 1114. In one example, the particular amount of time is based on a speed of movement of the point applicator 1100. In yet another embodiment, the discontinuity identification component 1114 can control the treatment composition component 1112 to stop depositing the treatment composition 1104 in response to the monitored absorbance level reaching the lower absorbance level 1124 (i.e., in response to the one or more parameters indicated that the reflection of light from the portion of skin 1106 no longer decreasing).

Figure 12A:
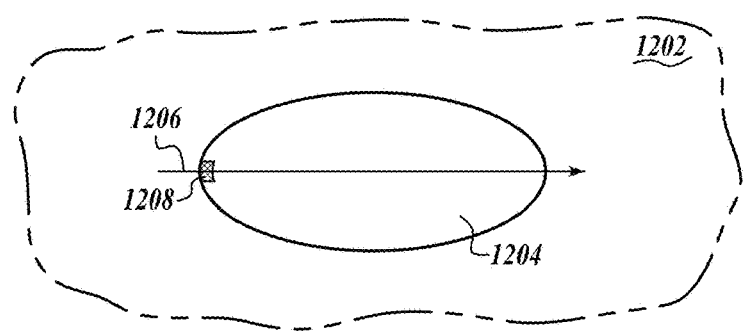
FIGS. 12A to 12C depict examples of treatment of a region of interest on a portion of skin using embodiments of the embodiments of point applicators described herein.
Figure 12B:
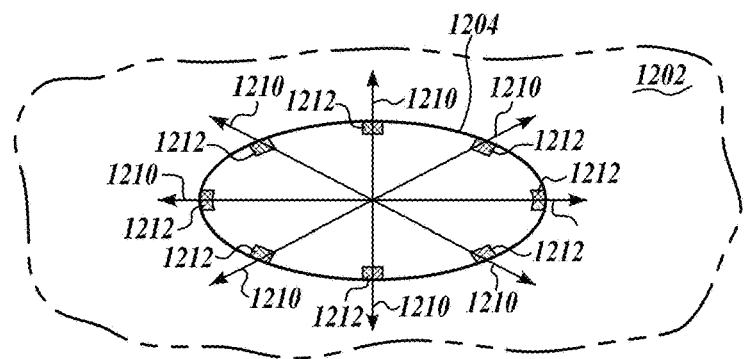
Figure 12C:
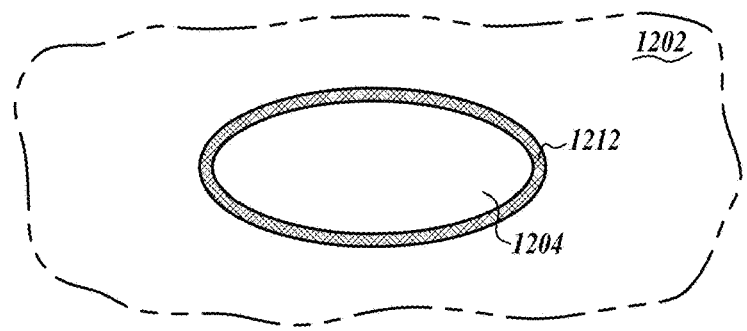

In one embodiment, the selectively depositing treatment composition in response to one or more parameters indicating a decrease in reflection of electromagnetic energy interrogation stimulus from the portion of skin is used to treat one or more edge portions of a region of interest on a portion of skin. FIGS. 12A to 12C depict examples of a portion of skin 1202 and a region of interest 1204 where a point applicator is used to treat one or more edge portions of the region of interest 1204. In FIG. 12A, the point applicator is moved in a single one-way direction 1206 over the region of interest 1204. As the point applicator approaches the edge of the region of interest 1204, the discontinuity identification component controls the treatment composition component to selectively deposit the treatment composition to the edge portion 1208 on the region of interest 1204 of the portion of skin 1202 based on one or more inputs indicative of a decrease in reflection of electromagnetic energy interrogation stimulus from the portion of skin 1202. The treatment composition component deposits an amount of the treatment composition on the edge portion 1208. In certain embodiments, the amount of the treatment composition is based a predetermined amount of the treatment composition, an amount of the treatment composition that is deposited during a predetermined amount of time, or any other amount of treatment composition.

FIG. 12B depicts an example of a point applicator moving over the region of interest 1204 in a plurality of two-way directions 1210. The point applicator encounters the region of interest 1204 a number of times and the point applicator deposits treatment composition on the edge portions 1212 each time the point applicator encounters the region of interest 1204. As shown in FIG. 12B, the edge portions 1212 cover a greater percentage of the total edge portion of the region of interest 1204 as the number of times and/or directions that the point applicator crosses the region of interest 1204 increases. FIG. 12C depicts an example of the treated edge portions 1212 covering the entire edge of the region of interest 1204, as would be the case if the number of times that the point applicator crosses the region of interest 1204 continued to increase.

Using the embodiments of point applicators described herein, different types of treatment compositions can be used. In one example, the treatment composition is a bleaching composition that bleaches the region of interest in the stratum corneum of the portion of skin. In the case where the point applicator treats the edges of the region of interest (e.g., as shown in FIG. 12C), the bleaching of the edges of the region of interest over successive treatments provides a user of the point applicator with a visual indication of how the treatment composition is working. In other words, each time the edge portions of the region of interest are treated with a bleaching composition, the overall size of the region of interest decreases, giving the user the sense that the treatment is continuing to be successful. In another example, the region of interest is below the stratum corneum of the portion of skin and the treatment composition is a composition configured to treat the region of interest.

The treatment composition component of embodiments of the point applicators described herein can take various forms. In one embodiment, the treatment composition component includes at least one nozzle and a propulsion device configured to propel a droplet of the treatment composition out of an outlet of the at least one nozzle. In some examples, the propulsion device includes a thermal propulsion device or a transducer propulsion device, such as those depicted in FIGS. 7 and 8. The treatment composition, in embodiments of point applicators described herein, is stored in a reservoir assembly that includes a reservoir of the treatment composition. When used in a point applicator, the reservoir assembly provides the treatment composition to the treatment composition component.

Figure 13:
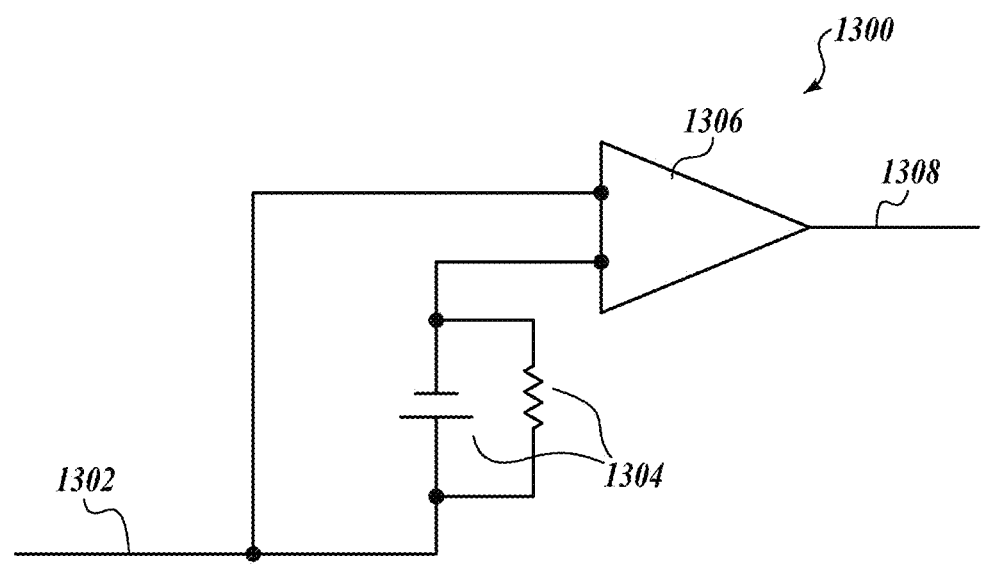
FIG. 13 depicts an embodiment of a passive controller that is usable in embodiments of the point applicators described herein.

FIG. 13 depicts an embodiment of a passive discontinuity identification component 1300 that is usable in embodiments of the point applicators described herein. The passive discontinuity identification component 1300 is passive in the sense that it does not need to be powered by an external power source to function. The passive discontinuity identification component 1300 receives an input signal 1302 from an electromagnetic energy detector. The input signal 1302 is passed in parallel to a phase delay circuit 1304 and to a comparator 1306. The comparator 1306 compares the input signal 1302 to the signal from the phase delay circuit 1304. The comparator 1306 functions to determine whether the input 1302 is decreasing. Such a comparison indicates whether the reflection of electromagnetic energy interrogation stimulus from the portion of skin at the deposit location is decreasing. The comparator generates an output signal 1308 indicative of whether the input signal 1302 is decreasing. The output signal 1308 is provided to a treatment composition component and the treatment composition component selectively deposits treatment composition based on the output signal 1308.

One benefit to having a passive discontinuity identification component in embodiments of the point applicators described herein is that the point applicator is operable with relatively low power requirements. The electromagnetic energy detector and the treatment composition component may require some power to operate, but the point applicator would not use as much power with a passive discontinuity identification component that the point applicator would use with a powered discontinuity identification component. Thus, one benefit of a passive discontinuity identification component is that the overall cost and complexity of the point applicator is reduced. Moreover, the point applicator may include a power source (e.g., one or more batteries) that is capable of powering the point applicator to dispense all of the treatment composition in the point applicator without recharging or replacing the power source.

Figure 14:
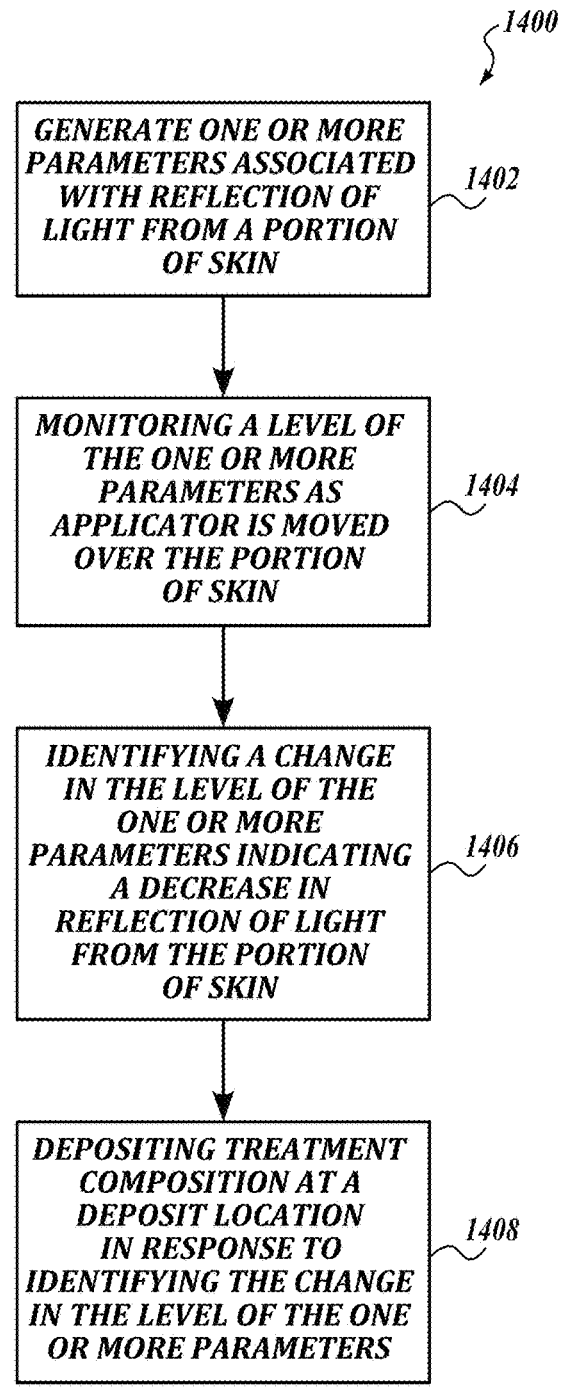
FIG. 14 depicts an embodiment of a method performed by embodiments of the embodiments of point applicators described herein.

Embodiments of point applicators described herein are capable of being used to perform a method 1400 depicted in FIG. 14. At box 1402, one or more parameters are generated where the one or more parameters generated are associated with reflection of light from a portion of skin as the applicator traverses the portion of skin. In one example, the one or more parameters are generated by an electromagnetic energy detector of an applicator. At block 1404, a level of the one or more parameters is monitored as the applicator traverses the portion of skin. In one example, the level of the one or more parameters is monitored by a discontinuity identification component of the applicator. At block 1406, one or more inputs are identified, indicating a decrease in reflection of light from the portion of skin at a deposit location. In one example, the change of the level of the one or more parameters is identified by the discontinuity identification component. At block 1408, treatment composition is deposited at the deposit location in response to the discontinuity identification component identifying the decrease in reflection of light from the portion of skin at a deposit location. In one example, the treatment composition is deposited by at least one treatment composition component of the applicator.

In some embodiments, the method 1400 includes additional steps described herein that are not depicted in FIG. 14. In other examples, the method 1400 includes one or more steps, such as depositing the treatment composition on the edge portion of the treatable region of interest on the portion of skin, moving the applicator over the treatable region of interest in a plurality of different directions to encounter a plurality of different edge portions of the treatable region of interest, identifying a change of the level of the one or more parameters when the applicator encounters each of the plurality of different edge portions of the treatable region of interest based on an indication of a decrease in reflection of light from the portion of skin at each of the plurality of different edge portions, and/or depositing the treatment composition on each of the plurality of different edge portions.

Embodiments of point applicators described herein are capable of being used to perform other methods. In one embodiment, a level of the one or more spectral parameters is monitored as an applicator traverses a portion of skin and delivery of a composition at the deposit location is actuated when the monitoring of the level of the one or more parameters as the applicator traverses the portion of skin is indicative that reflection of light from the portion of skin at a deposit location is decreasing. In one example, monitoring a level of the one or more parameters as the applicator traverses the portion of skin includes generating one or more parameters associated with reflection of light from a portion of skin as the applicator traverses a portion of skin. In another example, monitoring a level of the one or more parameters as the applicator traverses the portion of skin includes generating one or more parameters associated with reflection of light from a portion of skin as the applicator traverses the portion of skin. In another example, monitoring a level of the one or more parameters as the applicator traverses the portion of skin includes generating one or more parameters associated with spatially resolved spectra of the portion of skin. In another example, monitoring a level of the one or more parameters as the applicator traverses the portion of skin includes identifying a change in reflection of light from the portion of skin at a deposit location.

Imaging Applicator

The following discussion provides examples of systems, apparatuses, and methods for sensing and treating skin conditions using an imaging applicator that has an electromagnetic energy interrogation component and at least one treatment composition component. In one example, the electromagnetic energy interrogation component includes an illumination source that directs an electromagnetic energy stimulus toward a portion of skin and a detector that receives electromagnetic energy from the portion of skin in response to the electromagnetic energy stimulus directed toward the portion of skin by the illumination source. In one example, the at least one treatment composition component selectively deposits a treatment composition on the portion of skin. In another example, a characteristic of electromagnetic energy received by the electromagnetic energy interrogation component from the portion of skin is determined, the characteristic of electromagnetic energy received by the electromagnetic energy interrogation component from the portion of skin is determined to be associated with a treatable region of interest on the portion of skin, and the at least one treatment composition component is controlled to selectively deposit the treatment composition to at least a portion of the treatable region of interest on the portion of skin.

Figure 15A:
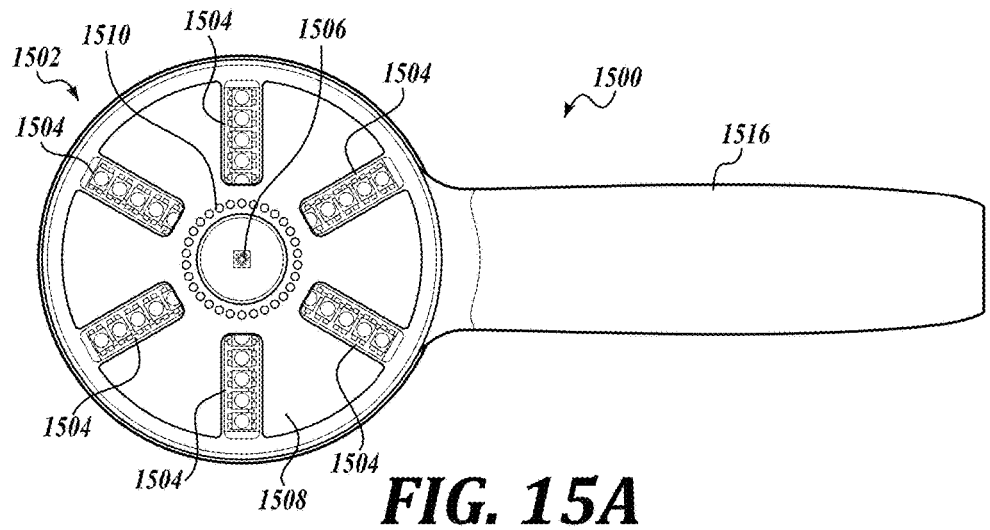
FIGS. 15A to 15C depict an embodiment of an imaging applicator used to treat a portion of skin.
Figure 15B:
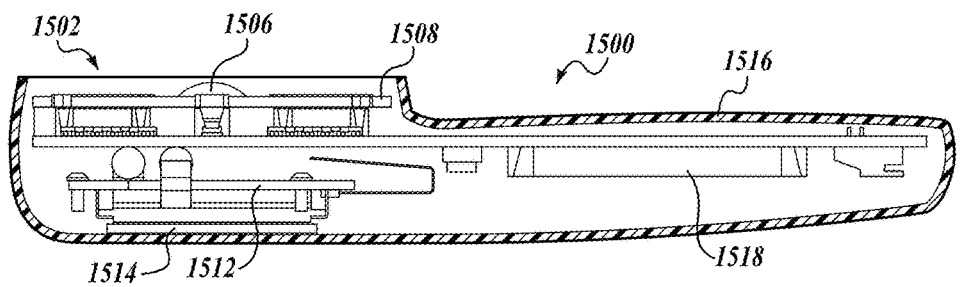
Figure 15C:
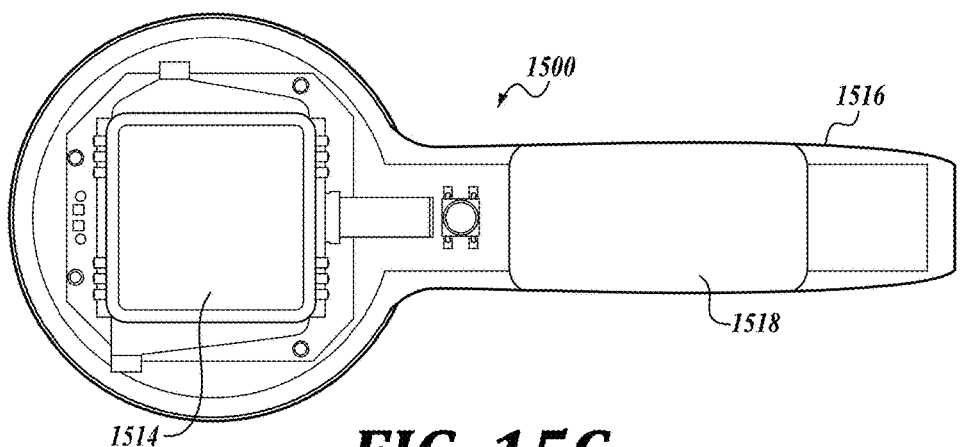

An embodiment of an applicator 1500 is depicted in FIGS. 15A to 15C. The applicator 1500 includes an electromagnetic energy interrogation component 1502 that includes an illumination source 1504 and a detector 1506. In the embodiment shown in FIG. 15A, the illumination source 1504 includes multiple sets of illumination sources, and each of the sets includes multiple individual illumination sources. The illumination source 1504 directs an electromagnetic energy stimulus toward a portion of skin. In one embodiment, the individual illumination sources are light sources, such as light emitting diodes (LEDs). In one embodiment, the illumination source 1504 emits electromagnetic energy at a plurality of different peak emission wavelengths. In another embodiment, the illumination source 1504 includes first illumination sources (e.g., one of the sets of illumination sources shown in FIG. 15A) that emit electromagnetic energy at a first wavelength and second illumination sources (e.g., another one of the sets of illumination sources shown in FIG. 15A) that emit electromagnetic energy at a second wavelength. In some embodiments, the illumination source 1504 is activated to produce narrow band illumination (e.g., at a particular color) or multiple combinations (e.g., at multiple wavelengths to produce simulated white light). When the illumination source 1504 is capable of directing electromagnetic energy in a wide range of wavelengths (either at individual wavelengths or at multiple wavelengths in the wide range), certain epidermal and dermal features will either absorb or fluoresce when exposed to particular wavelength ranges or mixtures.

The illumination source 1504 can take a number of forms. In one example, the illumination source 1504 includes one or more Group III-V (GaAs) based LEDs that are capable of emitting electromagnetic radiation at wavelengths in a range spanning from green visible light to near infrared. In another example, the illumination source 1504 includes one or more Group III-nitride blue LED solid state emitters that are capable of emitting electromagnetic radiation at wavelengths in a range spanning from ultraviolet to blue visible light. In one embodiment, the illumination source 1504 illuminates an area in a range of about one to three square centimeters. In some examples, the number of individual illumination sources (e.g., the number of LEDs) can be in a range from one to one hundred.

In one embodiment, the wavelength output of illumination source 1504 is selected based on the optical response desired from a particular skin condition. In one example, the wavelength output of illumination source 1504 includes one or more gallium-indium-nitrogen (GaInN) LEDs that have a wavelength output of about 360-370 nm. Such a wavelength output approximates the wavelength output a Wood's lamp examination tool (about 365 nm). In other embodiments, the illumination source 1504 emits electromagnetic energy in a range of wavelengths from about 200 nm to about 2000 nm. That range includes wavelengths in the ultraviolet range (about 350 nm) and near infrared (about 1200 nm).

The detector 1506 receives electromagnetic energy from the portion of skin in response to the electromagnetic energy stimulus directed toward the portion of skin by the illumination source 1504. The detector 1506 can take a number of forms. In one example, the detector 1506 includes an imager, such as an RGB camera, a CMOS camera, or a CCD camera. The detector 1506 has sufficient resolution to detect regions of interest on a portion of skin and has a size that permits inclusion in the imaging applicator 1500. In some embodiments, the detector 1506 discriminates color either by selective filtering or wavelength selective absorption within multiple photodetector layers. For example, a spectral absorption feature for a given chromophore in skin can be manifested as dark spots on an image with properly designed illumination. In a similar example, excited fluorophores exhibit distinct emission within a wavelength band.

The imaging applicator 1500 also includes a dispenser platform 1508 that includes treatment composition components 1510. While the particular embodiment shown in FIG. 15A includes multiple treatment composition components 1510, the dispenser platform 1508 could include only one treatment composition component. The treatment composition components 1510 selectively deposit treatment composition to portions of skin. In one embodiment, each of the treatment composition components 1510 includes at least one nozzle and a propulsion device configured to propel a droplet of the treatment composition out of an outlet of the at least one nozzle. In some examples, the propulsion device includes a thermal propulsion device or a transducer propulsion device, such as those depicted in FIGS. 7 and 8. In one embodiment, the treatment composition components 1510 are capable of depositing treatment composition on the portion of skin with an accuracy in a range from about ±25 µm to about ±200 µm. In another embodiment, the treatment composition components 1510 are made from materials that resist corrosion or degradation from off-neutral pH or organic solvent-based chemicals.

The imaging applicator 1500 also includes a discontinuity identification component 1512. In on example, the discontinuity identification component 1512 is a controller. The discontinuity identification component 1512 determines a treatment status based on an interrogation response to an electromagnetic energy stimulus. For example, the response to the electromagnetic energy stimulus is indicative of an absorption difference of greater than 20%. The treatment composition components 1510 selectively deposit a treatment composition on the portion of skin responsive to one or more inputs from the discontinuity component 1512 indicative of a target treatment status. In another example, the response to the electromagnetic energy stimulus is indicative of an absorption difference of greater than 40%. In another example, the interrogation response includes spatially resolved image information or temporally resolved image information. In another example, the discontinuity identification component 1512 is operably coupled to one or more electromagnetic energy transducers. In another example, the discontinuity identification component 1512 is operably coupled to one or more components having circuitry configured to acquire one or more spatially resolved images the portion of skin. In another example, the discontinuity identification component 1512 is operably coupled to one or more components having circuitry configured to acquire one or more temporally resolved images of the portion of skin. In yet another example, the discontinuity identification component 1512 includes one or more components having circuitry configured to classify an imaged object based on one or more inputs from the discontinuity identification component 1512 indicative of a target treatment status.

In another embodiment, the discontinuity identification component 1512 identifies a characteristic of electromagnetic energy received by the electromagnetic energy interrogation component 1502 from the portion of skin, determines whether the characteristic of electromagnetic energy received by the electromagnetic energy interrogation component 1502 from the portion of skin is associated with a treatable region of interest on the portion of skin, and controls the treatment composition components 1510 to selectively deposit the treatment composition to at least a portion of the treatable region of interest on the portion of skin. In one embodiment, the discontinuity identification component 1512 determines whether the characteristic of electromagnetic energy received by the electromagnetic energy interrogation component 1502 from the portion of skin is associated with a treatable region of interest on the portion of skin based on a set of absorbance and/or emission characteristics. Examples of such absorbance and/or emission characteristics include one or more of absorbance spectrum of hemoglobin, fluorescence of tryptophan, peptide near infrared vibrational overtone absorbance, melanin absorbance, water near infrared absorbance, keratin absorbance and fluorescence, or porphyrin fluorescence. In one example, the discontinuity identification component 1512 includes or has access to a library of absorbance and/or emission characteristics of various skin conditions. In one embodiment, the discontinuity identification component 1512 executes algorithms to determine the composition of skin features in an area of the portion of skin. In some examples, such algorithms include CMOS signal level detection and RGB color or grey level image analysis.

In one embodiment, the discontinuity identification component 1512 determines that the characteristic of electromagnetic energy received by the electromagnetic energy interrogation component is a particular wavelength. For example, the particular wavelength can be a wavelength in a particular range of electromagnetic energy (e.g., within an infrared range, within an ultraviolet range, within a range of a particular color of visible light, etc.). In another embodiment, the discontinuity identification component 1512 determines that the characteristic of electromagnetic energy received by the electromagnetic energy interrogation component is a peak received wavelength. For example, electromagnetic energy received by the electromagnetic energy interrogation component may have multiple peak wavelengths, and the discontinuity identification component 1512 can determine that the electromagnetic energy received by the electromagnetic energy interrogation component has a peak received wavelength at or about a particular wavelength. In one embodiment, the discontinuity identification component 1512 determines that the peak received wavelength and a transmitted wavelength of electromagnetic energy directed toward the portion of skin by the illumination source 1504 are the same (i.e., the same wavelength emitted toward the portion of skin by the illumination source 1504 is reflected back to the detector). In another embodiment, the discontinuity identification component 1512 determines that the peak received wavelength and a transmitted wavelength of electromagnetic energy directed toward the portion of skin by the illumination source 1504 are different. For example, certain regions of interest fluoresce at a fluorescence wavelength of electromagnetic energy in response to receiving electromagnetic energy at the transmitted wavelength from the illumination source 1504.

The imaging applicator 1500 also includes a display 1514. In the embodiment shown in FIGS. 15A to 15C, the display 1514 is arranged on the applicator 1500 in a direction that is different from a direction that electromagnetic energy is directed from the illumination source 1504. The display 1514 is controlled by a controller and is capable of displaying any type of information or image. In one embodiment, the display 1514 displays an indication of a reduction in size of the treatable region of interest from a time before a previous treatment of the treatable region of interest. In one example, the display 1514 displays an image of the current size of the treatable region of interest and an outline of the size of the region of interest before the last treatment. Seeing the change in the treatable region of interest from previous treatments may increase the likelihood that a user of the applicator 1500 will continue using the product. In another embodiment, the display 1514 displays an indication of the treatable region of interest based on the electromagnetic energy received by the electromagnetic energy interrogation component from the portion of skin. For example, the display 1514 displays an image of the treatable region of interest captured by the illumination source 1504. In one example, the indication of the treatable region of interest is an image of the treatable region of interest at a scale that is larger than an actual size of the treatable region of interest. In this example, the applicator 1500 functions as an electronic magnifying glass such that, when a user of the illumination source 1504 places the detector 1506 over a treatable region of interest, the user is able to view the treatable region of interest on the display 1514 at a scale that is larger than the actual size of the treatable region of interest. In one embodiment, the display 1514 reports various conditions to a user against baseline data. In one example, levels of hyperpigmentation and hemoglobin are reported to a user based on absorbance data relative to a user-stored historical baseline used to determine levels of erythema or melanin absorbance.

In the embodiment shown in FIGS. 15A to 15C, the applicator 1500 includes a handle 1516. The handle 1516 increases convenience for a user to use the applicator 1500. In one embodiment, the handle 1516 houses a treatment composition reservoir assembly 1518. In other embodiments, the handle 1516 houses additional components of the applicator, such as a power source (e.g., rechargeable battery), an electrical connection usable to recharge a power source, user input mechanisms (e.g., power buttons, buttons that activate the electromagnetic energy interrogation component 1502 and the treatment composition components 1510, etc.), indicators (e.g., a light indicating whether the applicator 1500 is operating), and the like.

In one embodiment, various treatment composition components 1510 of the applicator 1500 deposit different treatment compositions. In this embodiment, the discontinuity identification component 1512 controls which of the different treatment compositions are deposited on the portion of skin. In one example, the discontinuity identification component 1512 selects, from the plurality of treatment compositions, the treatment composition to be deposited on the portion of skin based in part on the characteristic of electromagnetic energy received by the electromagnetic energy interrogation component 1502 from the portion of skin. For example, when illuminated by the electromagnetic energy interrogation component 1502, the first type of region of interest will fluoresce at a different wavelength while a second type of region of interest will reflect back the same wavelength. The discontinuity identification component 1512 determines which treatment composition to deposit based on the wavelength received back (e.g., a treatment for the first type of region of interest if the fluorescence wavelength is received or a treatment for the second type of region of interest if the emission wavelength is received).

Figure 16:
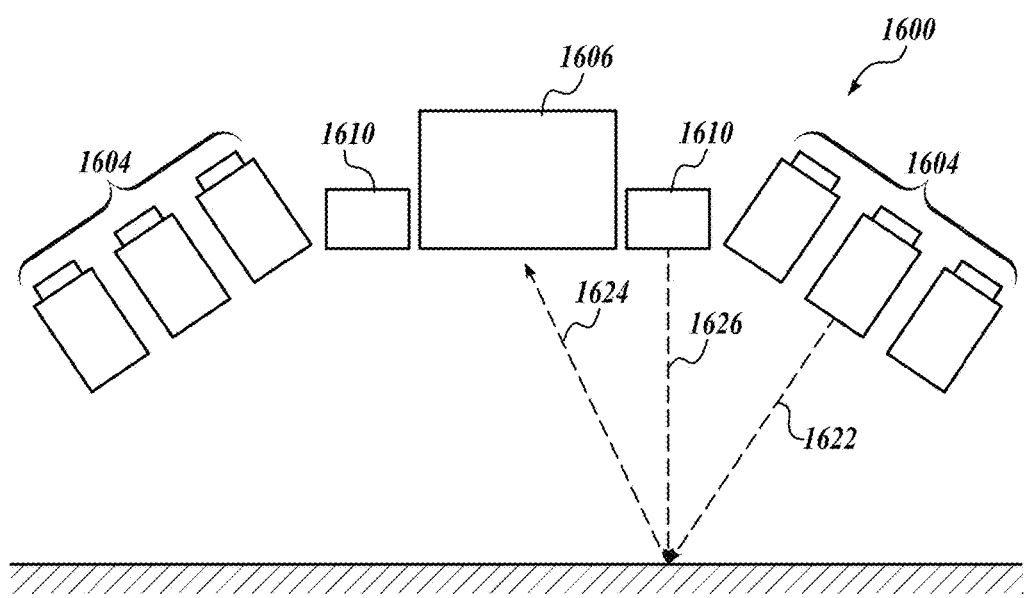
FIG. 16 depicts an example of functions performed by embodiments of the imaging applicators described herein.

An example of functions performed by an embodiment of an imaging applicator 1600 is depicted in FIG. 16. The imaging applicator 1600 can be the same or different from the imaging applicator 1500 depicted in FIGS. 15A to 15C. The imaging applicator 1600 includes an illumination source 1604, a detector 1606, and treatment composition components 1610. The imaging applicator 1600 is located over a portion of skin 1620. The illumination source 1604 directs an electromagnetic energy stimulus 1622 toward the portion of skin 1620. The detector 1606 receives electromagnetic energy 1624 from the portion of skin 1620 in response to the electromagnetic energy stimulus 1622 directed toward the portion of skin 1620 by the illumination source 1604. A controller (not shown) of the imaging applicator 1600 determines that a characteristic of the received electromagnetic energy 1624 is associated with a treatable region of interest on the portion of skin 1602. The controller controls selective depositing of a treatment composition 1626 by at least one of the treatment composition components 1610 to a portion of the treatable region of interest on the portion of skin 1620.

Figure 17A:
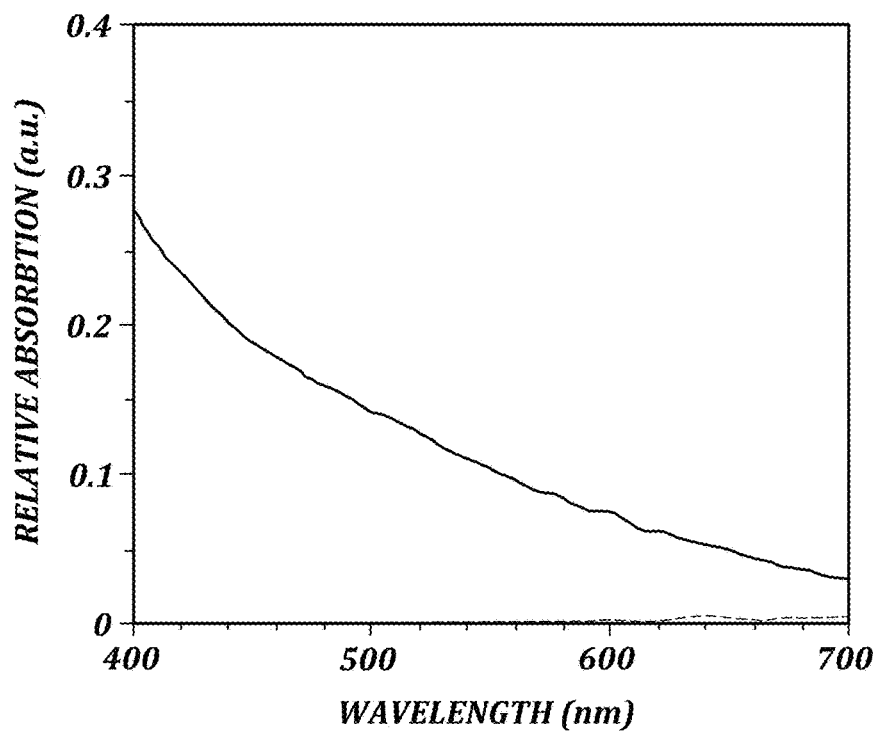
FIGS. 17A and 17B depict, respectively, a chart of absorbance by melanin and hyperpigmented areas imaged on a patient's skin.
Figure 17B:

Embodiments of the imaging applicators described herein have the benefit of being able to identify regions of interest that may not be visible to users. The appearance of smooth and uniform skin can be affected by a number of factors. Blemishes or patches can occur within the epidermis and dermis that are spatially distinct manifestations of any number of conditions. Everyday examples include pimples (open or closed comedones), hyperpigmentation (i.e., melasma), sun related age spots (solar lentigines), several types of benign keratosis, and the like. Solar lentigines and hyperpigmentation commonly form spots that can range from 0.2 mm to 3 mm in diameter. When fully developed, they are clearly apparent under broadband visible light illumination and dramatically evident under ultraviolet illumination at about 365 nm. This is due to that fact that age spots and hyperpigmentation possess higher concentrations of melanin in contrast to the surrounding, less pigmented, skin. As shown in the chart in FIG. 17A, melanin shows a monotonically increasing absorbance below 400 nm. Wavelength band pass filtering and polarization are usable to aid in detecting hyperpigmented areas on a portion of skin. As shown in the image in FIG. 17B, hyperpigmented areas imaged in high contrast against less pigmented adjacent regions depict regions of interest in detail. Moreover, early stage or nascent spots are much more discernable under narrow wavelength band ultraviolet illumination than under normal room lighting. Another example is the high concentration of porphyrins in comedones. Under ultraviolet excitation, porphyrins give strong fluorescence from the green to red portions of the visible spectrum. In general, such imaging not only offers a method for early detection of hyperpigmentation but also a number of dermatological and cosmetic conditions.

Figure 18:
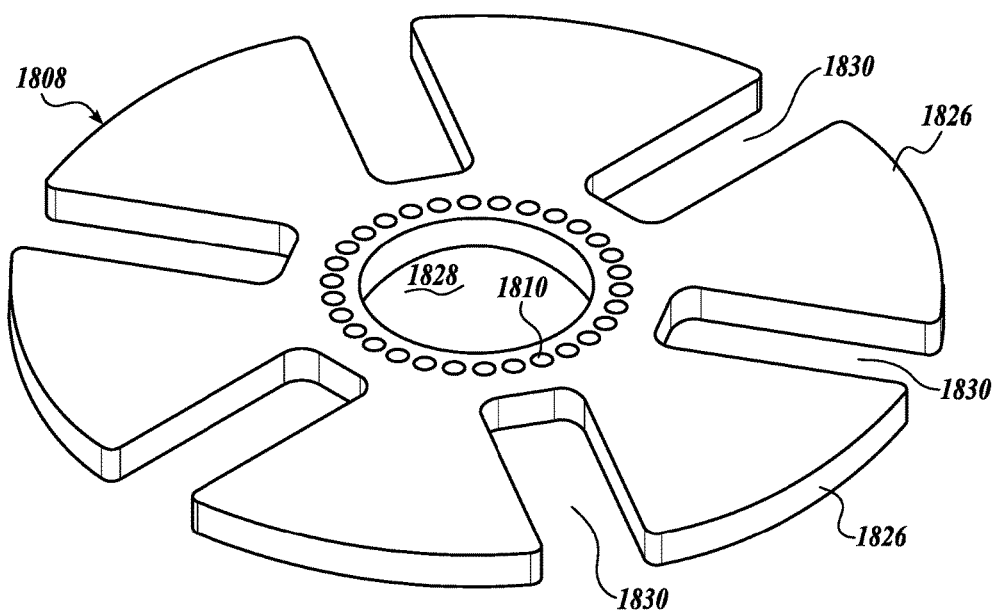
FIG. 18 depicts an embodiment of a dispenser platform that is usable in embodiments of the imaging applicators described herein.

FIG. 18 depicts an embodiment of a dispenser platform 1808 that is usable in embodiments of the imaging applicators described herein. The dispenser platform 1808 includes treatment composition components 1810. The dispenser platform 1808 also includes outer portions 1826 that are capable of holding treatment composition to serve as a reservoir for the treatment composition components 1810. In one embodiment, different outer portions 1826 hold different treatment compositions. In another embodiment, each of the treatment composition components 1810 is separately controllable by the controller. In the embodiment shown in FIG. 18, the dispenser platform 1808 includes a central void 1828 and outer voids 1830. In one embodiment, the central void 1828 permits a space for a detector and the outer voids 1830 permit spaces for illumination sources.

Figure 19:
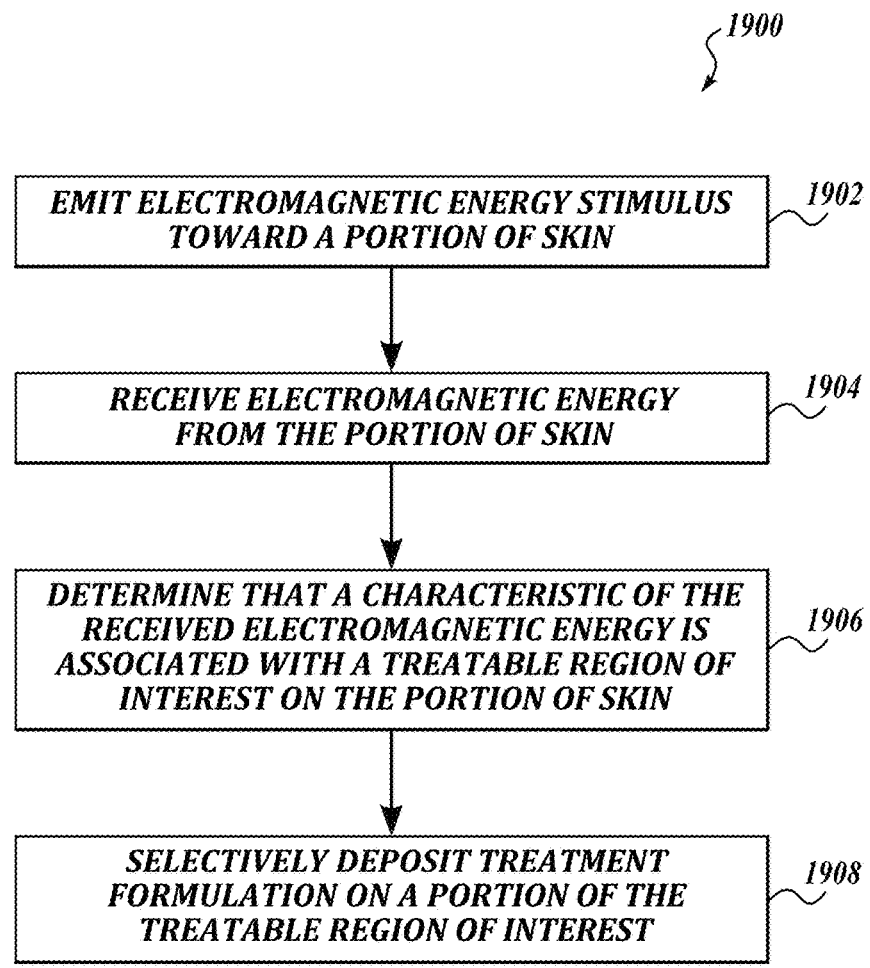
FIG. 19 depicts an embodiment of a method performed by embodiments of the imaging applicators described herein.

Embodiments of point applicators described herein are capable of being used to perform a method 1900 depicted in FIG. 19. At block 1902, an electromagnetic energy stimulus is emitted toward a portion of skin. In one example, the electromagnetic energy stimulus is emitted toward a portion of skin by an electromagnetic energy interrogation component of the applicator. At block 1904, electromagnetic energy is received from the portion of skin in response to the electromagnetic energy stimulus directed toward the portion of skin by the illumination source. In one example, the electromagnetic energy is received by the electromagnetic energy interrogation component of the applicator. At block 1906, a characteristic of the electromagnetic energy received by the electromagnetic energy interrogation component from the portion of skin is determined to be associated with a treatable region of interest on the portion of skin. In one example, a controller of the applicator determines that the characteristic of the electromagnetic energy received by the electromagnetic energy interrogation component from the portion of skin is associated with the treatable region of interest on the portion of skin. At block 1908, a treatment composition is selectively deposited to at least a portion of the treatable region of interest on the portion of skin. In one example, the treatment composition is selectively deposited by at least one treatment composition component of the applicator.

In some embodiments, the method 1900 includes additional steps described herein that are not depicted in FIG. 19. In one example, the method 1900 includes determining a difference between the characteristic of electromagnetic energy received by the electromagnetic energy interrogation component from the portion of skin and a corresponding characteristic of the electromagnetic energy stimulus emitted toward a portion of skin. In another example, the method 1900 includes determining a baseline characteristic of the portion of skin. Determining the baseline characteristic of the portion of skin is helpful in determining portions of skin that do not include regions of interest so that treatment composition deposited outside of regions of interest is kept at a minimum. In another example, the method 1900 includes determining a difference between the characteristic of electromagnetic energy received by the electromagnetic energy interrogation component from the portion of skin and the baseline characteristic of the portion of skin.

Embodiments of point applicators described herein are capable of being used to perform other methods. In one embodiment, an electromagnetic energy response is received from a portion of skin interrogated with an electromagnetic energy stimulus and discontinuity identification information is determined responsive to receiving the electromagnetic energy response from the portion of skin. A treatment composition is selectively deposited to a region of interest on the portion of skin when determining discontinuity identification information is indicative of a target treatment status.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. An applicator, comprising:
   a discontinuity identification component operably coupled to an electromagnetic energy interrogation component, the discontinuity identification component configured to determine a treatment status to selectively deposit a treatment composition based on an interrogation response to an electromagnetic energy stimulus indicative of an absorption difference of greater than a target amount, and configured to stop deposition of the treatment composition when the absorption difference is less than the target amount, the absorption difference being a difference in the absorption measured from a treatable region on a portion of skin compared to a measured baseline absorption of a non-treatable region of skin; and
   at least one treatment composition component operably coupled to the discontinuity identification component, the at least one treatment composition component configured to selectively deposit and stop deposition of a treatment composition on the portion of skin responsive to one or more inputs from the discontinuity identification component indicative of a target treatment status.

2. The applicator of claim 1, wherein an interrogation response includes spatially resolved image information, or temporally resolved image information.

3. The applicator of claim 1, wherein the absorption difference is greater than 20%.

4. The applicator of claim 1, wherein the discontinuity identification component is operably coupled to one or more electromagnetic energy transducers.

5. The applicator of claim 1, wherein the discontinuity identification component is operably coupled to one or more components having circuitry configured to acquire one or more spatially resolved images of the portion of skin.

6. The applicator of claim 1, wherein the discontinuity identification component is operably coupled to one or more components having circuitry configured to acquire one or more temporally resolved images of the portion of skin.

7. The applicator of claim 1, wherein the discontinuity identification includes one or more components having circuitry configured to classify an imaged object based on one or more inputs from the discontinuity component indicative of the target treatment status.

8. The applicator of claim 1, wherein the electromagnetic energy interrogation component is configured to receive electromagnetic energy at a fluorescence wavelength, wherein a region of interest is capable of fluorescing at a fluorescence wavelength in response to stimulation by the applicator.

9. The applicator of claim 1, wherein the applicator includes an illumination source configured to emit electromagnetic energy at a plurality of different peak emission wavelengths.

10. The applicator of claim 1, wherein the applicator includes an illumination source that includes a first plurality of illumination sources configured to emit electromagnetic energy at a first wavelength and a second plurality of illumination sources configured to emit electromagnetic energy at a second wavelength.

11. The applicator of claim 1, further comprising:
a display arranged on the applicator in a direction that is different from a direction that electromagnetic energy is directed from an illumination source.

12. The applicator of claim 11, wherein the display is configured to display an indication of a reduction in size of a treatable region of interest from a time before a previous treatment of the treatable region of interest.

13. The applicator of claim 11, wherein the display is configured to display an indication of a treatable region of interest based on the electromagnetic energy received by the electromagnetic energy interrogation component from the portion of skin.

14. The applicator of claim 13, wherein the indication of the treatable region of interest is an image of the treatable region of interest at a scale that is larger than an actual size of the treatable region of interest.

15. The applicator of claim 1, wherein the at least one treatment composition component includes a plurality of treatment components configured to selectively deposit a plurality of treatment compositions.

16. The applicator of claim 13, wherein the discontinuity identification component is further configured to select, from the plurality of treatment compositions, the treatment composition to be deposited on the portion of skin based in part on the characteristic of electromagnetic energy received by an imaging component from the portion of skin.

17. The applicator of claim 1, wherein an illumination source is configured to emit electromagnetic energy in a range from about 200 nm to about 2000 nm.

18. A method of treating a portion of skin using an applicator, the method comprising:

receiving an electromagnetic energy response from the portion of skin interrogated with an electromagnetic energy stimulus;
determining discontinuity identification information responsive to receiving the electromagnetic energy response from the portion of skin; and
selectively depositing and stopping a treatment composition to a region of interest on the portion of skin when determining discontinuity identification information is indicative of a target treatment status based on a difference in absorption measured from the treatable region of interest compared to a measured baseline absorption of a non-treatable region.

19. The method of claim 18, wherein the method includes determining that the electromagnetic energy response from the portion of skin is associated with a treatable region of interest on the portion of skin and determining a difference between a characteristic of the electromagnetic response from the portion of skin and a corresponding characteristic of electromagnetic energy stimulus emitted toward the portion of skin.

20. The method of claim 19, wherein the difference between the electromagnetic energy response from the portion of skin and the corresponding characteristic of the electromagnetic energy stimulus emitted toward the portion of skin is one or more of a difference in wavelength or a difference in color.

21. The method of claim 18, further comprising:
determining a baseline characteristic of the portion of skin.

22. The method of claim 21, wherein the method includes determining a difference between the electromagnetic energy response from the portion of skin and the baseline characteristic of the portion of skin.

* * * * *